United States Patent
Cao et al.

(10) Patent No.: US 9,845,238 B2
(45) Date of Patent: Dec. 19, 2017

(54) NANONOZZLE DEVICE ARRAYS: THEIR PREPARATION AND USE FOR MACROMOLECULAR ANALYSIS

(71) Applicant: BioNano Genomics, Inc., San Diego, CA (US)

(72) Inventors: Han Cao, San Diego, CA (US); Parikshit A. Deshpande, San Diego, CA (US); Michael David Austin, San Diego, CA (US); Michael Boyce-Jacino, San Diego, CA (US)

(73) Assignee: BioNano Genomics, Inc., San Diego, CA (US)

( * ) Notice: Subject to any disclaimer, the term of this patent is extended or adjusted under 35 U.S.C. 154(b) by 0 days.

(21) Appl. No.: 14/712,816

(22) Filed: May 14, 2015

(65) Prior Publication Data

US 2015/0323518 A1 Nov. 12, 2015

Related U.S. Application Data

(62) Division of application No. 12/374,141, filed as application No. PCT/US2007/016408 on Jul. 19, 2007, now Pat. No. 9,061,901.

(60) Provisional application No. 60/831,772, filed on Jul. 19, 2006, provisional application No. 60/908,582, filed on Mar. 28, 2007, provisional application No. 60/908,584, filed on Mar. 28, 2007.

(51) Int. Cl.
| | |
|---|---|
| *C12Q 1/68* | (2006.01) |
| *B82Y 30/00* | (2011.01) |
| *G01N 27/447* | (2006.01) |
| *B01L 3/00* | (2006.01) |
| *G01N 33/487* | (2006.01) |
| *G01N 35/10* | (2006.01) |

(52) U.S. Cl.
CPC ......... *B82Y 30/00* (2013.01); *B01L 3/502761* (2013.01); *C12Q 1/6869* (2013.01); *G01N 27/447* (2013.01); *G01N 33/48721* (2013.01); *B01L 2200/0663* (2013.01); *B01L 2200/12* (2013.01); *B01L 2300/0645* (2013.01); *B01L 2300/0816* (2013.01); *B01L 2300/0822* (2013.01); *B01L 2300/0896* (2013.01); *B01L 2400/0415* (2013.01); *B01L 2400/0487* (2013.01); *G01N 2035/1039* (2013.01); *Y10T 436/143333* (2015.01); *Y10T 436/2575* (2015.01)

(58) Field of Classification Search
CPC ........ B01L 3/50; Y10T 436/2575; C12Q 1/68
See application file for complete search history.

(56) References Cited

U.S. PATENT DOCUMENTS

| | | | |
|---|---|---|---|
| 5,079,169 | A | 1/1992 | Chu et al. |
| 5,314,829 | A | 5/1994 | Coles |
| 5,356,776 | A | 10/1994 | Kambara et al. |
| 5,405,519 | A | 4/1995 | Schwartz |
| 5,427,663 | A | 6/1995 | Austin et al. |
| 5,599,664 | A | 2/1997 | Schwartz |
| 5,637,458 | A | 6/1997 | Frankel et al. |
| 5,720,928 | A | 2/1998 | Schwartz |
| 5,837,115 | A | 11/1998 | Austin et al. |
| 5,867,266 | A | 2/1999 | Craighead |
| 5,912,126 | A | 6/1999 | Darzynkiewicz |
| 6,117,634 | A | 9/2000 | Langmore |
| 6,147,198 | A | 11/2000 | Schwartz |
| 6,150,089 | A | 11/2000 | Schwartz |
| 6,174,671 | B1 | 1/2001 | Anantharaman et al. |
| 6,197,557 | B1 | 3/2001 | Makarov et al. |
| 6,210,896 | B1 | 4/2001 | Chan et al. |
| 6,214,246 | B1 | 4/2001 | Craighead |
| 6,221,592 | B1 | 4/2001 | Schwartz et al. |
| 6,263,286 | B1 | 7/2001 | Gilmanshin et al. |
| 6,340,567 | B1 | 1/2002 | Schwartz et al. |
| 6,344,319 | B1 | 2/2002 | Bensimon et al. |
| 6,355,420 | B1 | 3/2002 | Chan |
| 6,403,311 | B1 | 6/2002 | Chan |
| 6,438,279 | B1 | 8/2002 | Craighead et al. |
| 6,464,842 | B1 | 10/2002 | Golovchenko et al. |
| 6,607,888 | B2 | 8/2003 | Schwartz et al. |
| 6,627,067 | B1 | 9/2003 | Branton et al. |
| 6,635,163 | B1 | 10/2003 | Han et al. |
| 6,696,022 | B1 | 2/2004 | Chan et al. |
| 6,753,200 | B2 | 6/2004 | Craighead et al. |
| 6,762,059 | B2 | 7/2004 | Chan et al. |
| 6,772,070 | B2 | 8/2004 | Gilmanshin et al. |
| 6,790,671 | B1 | 9/2004 | Austin |
| 6,927,065 | B2 | 8/2005 | Chan et al. |
| 7,217,562 | B2 | 5/2007 | Cao et al. |
| 7,262,859 | B2 | 8/2007 | Larson et al. |

(Continued)

FOREIGN PATENT DOCUMENTS

| | | |
|---|---|---|
| CN | 1379857 A | 11/2002 |
| EP | 0497272 A1 | 8/1992 |

(Continued)

OTHER PUBLICATIONS

Office Action dated Jul. 7, 2015 in Japanese patent application No. 2014-089510.
Examination Report dated Nov. 9, 2012 in Australian Application No. 2008232616.
Office Action dated Apr. 16, 2015 in U.S. Appl. No. 14/195,474.
Examination Report dated Dec. 23, 2010 for European Application No. 08744609.2.
Office Action dated Sep. 25, 2012 for Japanese Application 2010-501259.

(Continued)

*Primary Examiner* — Narayan Bhat
(74) *Attorney, Agent, or Firm* — Knobbe, Martens, Olson & Bear, LLP

(57) ABSTRACT

Constricted nanochannel devices suitable for use in analysis of macromolecular structure, including DNA sequencing, are disclosed. Also disclosed are methods for fabricating such devices and for analyzing macromolecules using such devices.

22 Claims, 9 Drawing Sheets

(56) References Cited

U.S. PATENT DOCUMENTS

| | | |
|---|---|---|
| 7,282,330 B2 | 10/2007 | Zhao et al. |
| 7,312,033 B2 | 12/2007 | Accola et al. |
| 7,316,769 B2 | 1/2008 | Craighead et al. |
| 7,351,538 B2 | 4/2008 | Fuchs et al. |
| 7,371,520 B2 | 5/2008 | Zhao et al. |
| 7,402,422 B2 | 7/2008 | Fuchs et al. |
| 7,427,343 B2 | 9/2008 | Han et al. |
| 7,670,770 B2 | 3/2010 | Chou et al. |
| 7,771,944 B2 | 8/2010 | Xiao et al. |
| 7,775,368 B2 | 8/2010 | Schwartz et al. |
| 7,831,392 B2 | 11/2010 | Antoniotti et al. |
| 7,833,398 B2 | 11/2010 | Craighead et al. |
| 7,918,979 B2 | 4/2011 | Han et al. |
| 7,960,105 B2 | 6/2011 | Schwartz et al. |
| 8,137,569 B2 | 3/2012 | Harnack et al. |
| 8,168,380 B2 | 5/2012 | Chan et al. |
| 8,628,919 B2 | 1/2014 | Xiao et al. |
| 8,663,780 B2 | 3/2014 | Harnack et al. |
| 8,722,327 B2 | 5/2014 | Cao et al. |
| 9,061,901 B2 | 6/2015 | Cao et al. |
| 2001/0055764 A1 | 12/2001 | Empedocles et al. |
| 2002/0110818 A1 | 8/2002 | Chan |
| 2002/0119455 A1 | 8/2002 | Chan |
| 2002/0123063 A1 | 9/2002 | Gjerde et al. |
| 2002/0197639 A1 | 12/2002 | Shia et al. |
| 2003/0059822 A1 | 3/2003 | Chan et al. |
| 2003/0066749 A1 | 4/2003 | Golovchenko et al. |
| 2003/0104428 A1 | 6/2003 | Branton et al. |
| 2003/0162181 A1 | 8/2003 | Yang et al. |
| 2003/0209314 A1 | 11/2003 | Guo et al. |
| 2003/0219792 A1 | 11/2003 | Armes et al. |
| 2003/0219805 A1 | 11/2003 | Kelman et al. |
| 2003/0232346 A1 | 12/2003 | Su |
| 2003/0235854 A1 | 12/2003 | Chan et al. |
| 2004/0009612 A1 | 1/2004 | Zhao et al. |
| 2004/0033515 A1 | 2/2004 | Cao et al. |
| 2004/0166025 A1 | 8/2004 | Chan |
| 2004/0195098 A1 | 10/2004 | Broadley et al. |
| 2004/0197843 A1 | 10/2004 | Chou et al. |
| 2005/0082204 A1 | 4/2005 | Schwartz et al. |
| 2005/0208538 A1 | 9/2005 | Kurn et al. |
| 2005/0234656 A1 | 10/2005 | Schwartz et al. |
| 2005/0250117 A1 | 11/2005 | Su et al. |
| 2006/0011862 A1 | 1/2006 | Bernstein |
| 2006/0014181 A1 | 1/2006 | Barton |
| 2006/0068440 A1 | 3/2006 | Chan et al. |
| 2006/0073489 A1 | 4/2006 | Li et al. |
| 2006/0088944 A1 | 4/2006 | Schwartz et al. |
| 2006/0199202 A1 | 9/2006 | Lyamichev et al. |
| 2006/0275806 A1 | 12/2006 | Schwartz et al. |
| 2006/0275911 A1 | 12/2006 | Wang et al. |
| 2007/0128083 A1 | 6/2007 | Yantz |
| 2007/0161028 A1 | 7/2007 | Schwartz et al. |
| 2007/0219367 A1 | 9/2007 | Shchepinov et al. |
| 2008/0003689 A1 | 1/2008 | Lee |
| 2008/0085552 A1 | 4/2008 | Larson et al. |
| 2008/0103296 A1 | 5/2008 | Zhao |
| 2008/0242556 A1 | 10/2008 | Cao et al. |
| 2008/0254549 A1 | 10/2008 | Fuchs |
| 2009/0076735 A1 | 3/2009 | Briska et al. |
| 2009/0104611 A1 | 4/2009 | Schwartz et al. |
| 2009/0208950 A1 | 8/2009 | Briska |
| 2009/0317804 A1 | 12/2009 | Briska |
| 2010/0028886 A1 | 2/2010 | Briska |
| 2011/0171634 A1 | 7/2011 | Xiao |
| 2011/0171741 A1 | 7/2011 | Wang et al. |
| 2011/0210272 A1 | 9/2011 | Chan et al. |
| 2011/0306504 A1 | 12/2011 | Xiao et al. |
| 2012/0196382 A1 | 8/2012 | Chan et al. |
| 2012/0217161 A1 | 8/2012 | Chan et al. |
| 2012/0237936 A1 | 9/2012 | Xiao et al. |
| 2013/0177902 A1 | 7/2013 | Xiao et al. |
| 2013/0240357 A1 | 9/2013 | Xiao et al. |
| 2014/0030705 A1 | 1/2014 | Deshpande et al. |
| 2014/0221218 A1 | 8/2014 | Cao et al. |
| 2014/0249039 A1 | 9/2014 | Cao et al. |
| 2015/0368706 A1 | 12/2015 | Cao et al. |
| 2016/0097092 A1 | 4/2016 | Xiao et al. |
| 2016/0168621 A1 | 6/2016 | Xiao et al. |
| 2016/0289756 A1 | 10/2016 | Cao et al. |

FOREIGN PATENT DOCUMENTS

| | | |
|---|---|---|
| JP | 2001-507929 | 6/2001 |
| JP | 2003-507026 | 2/2003 |
| JP | 2004-147658 | 5/2004 |
| JP | 2005-505754 | 2/2005 |
| JP | 2005-518215 | 6/2005 |
| JP | 2005-524413 | 8/2005 |
| JP | 2005-527220 | 9/2005 |
| JP | 2005-532822 | 11/2005 |
| JP | 2005-533636 | 11/2005 |
| JP | 2006-521786 | 9/2006 |
| JP | 2007-500363 | 1/2007 |
| WO | WO 98/35012 A | 8/1998 |
| WO | WO 98/39485 | 9/1998 |
| WO | WO 00/79257 | 12/2000 |
| WO | WO 01/09184 | 2/2001 |
| WO | WO 01/13088 A | 2/2001 |
| WO | WO 0113088 A1 | 2/2001 |
| WO | WO 02/065138 | 8/2002 |
| WO | WO 02/099398 | 12/2002 |
| WO | WO02/099398 | 12/2002 |
| WO | WO 02/101095 | 12/2002 |
| WO | WO 03/010289 A2 | 2/2003 |
| WO | WO 03/072805 A2 | 9/2003 |
| WO | WO 03/106620 A2 | 12/2003 |
| WO | WO 03/106693 | 12/2003 |
| WO | WO 2005/065321 | 7/2005 |
| WO | WO 2005/078137 | 8/2005 |
| WO | WO2005078137 | 8/2005 |
| WO | WO 2006/102321 | 9/2006 |
| WO | WO 2007/065025 | 6/2007 |
| WO | WO 2008/076948 | 6/2008 |
| WO | WO 2010/002883 | 6/2009 |
| WO | WO 2010/002883 | 1/2010 |
| WO | WO 2010/053980 | 5/2010 |
| WO | WO 2010/059731 A2 | 5/2010 |
| WO | WO 2011/050147 | 4/2011 |

OTHER PUBLICATIONS

Patent Examination Report No. 1 dated Feb. 10, 2015 in Australian patent application No. 2009267086.
Office action dated Nov. 6, 2014 in U.S. Appl. No. 13/765,353.
Office action dated Apr. 21, 2015 in U.S. Appl. No. 13/765,353.
Office action dated Aug. 20, 2015 in U.S. Appl. No. 13/765,353.
Office Action dated Oct. 25, 2013, in U.S. Appl. No. 13/129,634.
Office Action dated Jun. 6, 2014, in U.S. Appl. No. 13/129,634.
Office Action dated Jan. 2, 2015 in U.S. Appl. No. 13/129,634.
Patent Examination Report No. 1 dated Aug. 21, 2015 in Australian patent application No. 2009316628.
Office Action dated Sep. 11, 2015 in Chinese Patent Application No. 201180060380.2.
Examination Report dated Jun. 24, 2015 in European patent application No. 11777058.1.
Office Action in U.S. Appl. No. 13/880,365, dated May 4, 2015.
Notification on Non-Compliance with the Unity of Invention Requirement dated Sep. 7, 2015 in Russian patent application No. 2013117936.
Office Action dated Jul. 14, 2015 in U.S. Appl. No. 13/710,180.
Official Action dated Dec. 22, 2014 in Russian patent application No. 2012116604.
Second Office Action dated Dec. 9, 2014 in Chinese Patent Application No. 201310054745.1.
Office Action dated May 29, 2015 for Chinese Patent Application No. 201310189106.6.
Office Action dated Sep. 17, 2014 for Chinese Patent Application No. 200980125335.3.
Office Action dated Apr. 3, 2015 for Chinese Patent Application No. 200980125335.3.

(56) References Cited

OTHER PUBLICATIONS

Amann R et al.: "In situ visualization of high genetic diversity in a natural microbial community", Journal of Bacteriology, American Society for Microbiology, Washington, DC; US, vol. 178, No. 12, Jun. 1, 1996, pp. 3496-3500.
W. Volkmuth et al.: "Observation of Electrophoresis of Sincle DNA Molecules in Nanofabricated Arrays", American Society for Biochemistry and Molecular Biology Biophysical Society Joint Meeting, Houston Texas, Feb. 9-13, 1992, Abstracts, FASEB Journal, vol. 6, No. 1, Jan. 1, 1992. 3 pages.
Austin et al.: "Scanning the Controls: Genomics and Nanotechnogloy," IEEE Transactions on Nanotechnology 1: 12-18, 2002.
Cai et al.: "Ordered restriction endonuclease maps of artificial chromosomes created by optical mapping on surfaces," PNAS 92: 5164-8, 1995.
Cai et al.: "High-resolution restriction maps of bacterial artificial chromosomes constructed by optical mapping." Proc. Natl. Acad. Sci. USA, vol. 95, No. 7, pp. 3390-3395 (1998).
Cao et al.: "Fabrication of 10 nm enclosed nanofluidic channels," Applied Physics Letters, 81(1):174-176 (2002).
Cao et al.: "Gradient nanostructures for interfacing microfluidics and nanofluidics," Applied Physics Letters, AIP, American Institute of Physics, Melville, NY, vol. 81, No. 16, pp. 3058-3060 (2002).
Castro et al.: "Single-molecule detection of specific nucleic acid sequences in unamplified genomic DNA." Analytical Chemistry, 69(19):3915-3920 (1997).
Chan et al.: "DNA mapping using microfluidic stretching and single molecule detection of fluorescent site-specific tags," Genome Research 14: 1137-1146, 2004.
Chan et al.: "DNA mapping using microfluidic stretching and single-molecule detection of fluorescent site-specific tags." Genome Research, 14(6):1137-1146 (2004).
Chang et al.: "DNA-Mediated Fluctuations in Ionic Current through Silicon Oxide Nanopore Channels," Nano Letters 4: 1551-1556, 2004.
Chen et al.: "Atomic Layer Deposition to Fine-Tune the surface Properties and Diameters of Fabricated Nanopores," Nano Letters 4: 1333-1337, 2004.
Chen et al.: "Probing Single DNA Molecule Transport Using Fabricated Nanopores," Nano Letters 4: 2293-2298, 2004.
Chinese Office Action dated Jun. 29, 2012 for Chinese Patent Application No. 200880017550.7.
Chinese Office Action dated Mar. 13, 2013 for Chinese Patent Application No. 200980154567.1.
Chinese Office Action dated Nov. 14, 2012 for Chinese Patent Application No. 200880017550.7.
Chinese Office Action dated Nov. 21, 2013 for Chinese Patent Application No. 200980154567.1.
Chou et al.: "A Microfabricated Device for Sizing and Sorting DNA Molecules," Proc. Natl. Acad. Sci. USA, Jan. 1999, 96, 11-13.
Conrad et al.: "A high-resolution survey of deletion polymorphism in the human genome," Nature Genetics 38: 75-81, 2006.
Czaplewski et al.: "Nanofluidic channels with elliptical cross sections formed using a nonlithographic process," Applied Physics Letters, Dec. 8, 2003, 83(23), 836-4838.
Das et al.: "Single molecule linear analysis of DNA in nano-channel labeled with sequence specific fluorescent probes", Nucleic Acids Research, 2010, vol. 38, o. 18, 8 pages.
Deamer et al.: "Characterization of Nucleic Acids by Nanopore Analysis," Acc Chem Res 35: 817-825, 2002.
Deegan et al.: "Contact line deposits in an evaporating drop," Physical Review E, Jul. 2000, 62(1), 756-765.
Dietrich et al.: "Advances in the Development of a Novel Method to be used in Proteomics using Gold Nanobeads," U/trasens/tive and Single-Molecule etection Technologies, edited by Jorg Enderlein, et al, Proc. of SPIE vol. 6092, 6092C (2006).
Eichler: "Widening the spectrum of human genetic variation," Nature Genetics 38: 9-11, 2006.

European Extended Search Report dated Jun. 18, 2014 for European Patent Application No. 13150068.8.
European Office Action dated Aug. 14, 2012 for European Patent Application No. 09760398.9.
European Office Action dated Oct. 18, 2013 for European patent application No. 09774334.8.
European Partial Search Report dated Feb. 5, 2014 for European Application No. EP 13150068.8.
European Search Report dated May 31, 2013 for European Application No. EP 12194842.6.
Examination Report dated Jul. 23, 2012 for European Application No. 08744609.2.
Extended European Search Report dated Oct. 22, 2013 for European patent application No. 13179160.0.
FDA Redbook 2000 Genotoxicity Tests, available at www.cfsan.fda.gov.
Final Decision of Rejection dated Aug. 13, 2013 for Japanese Application 2010-501259.
Fu et al.: "Sequencing Double-Stranded DNA by Strand Displacement", Nucleic Acids Research, Information Retrieval Ltd., vol. 25, No. 3, (Jan. 1997), pp. 677-679.
Gad et al.: "Bar code screening on combed DNA for large rearragements of the BRCA1 and BRCA2 genes in French breast cancerfamilies." J Med Genet 39: 17-21, 2002.
Gad et al.: "Color bar coding the BRCA1 gene on combed DNA: A useful strategy for detecting large gene arrangements." Genes, Chromosomes and Cancer 31: 5-84, 2001.
Gracheva et al.: "Simulation of the electric response of DNA translocation through a semiconductor nanopore-capacitor," Nanotechnology 17: 622-633, 2006.
Guidance for industry S2B Genotoxicity: A standard Battery for Genotoxicity Testing of Pharmaceuticals, Jul. 1997, ICH.
Guo et al: "Fabrication of Size-Controllable Nanofluidic Channels by Nanoimprinting and its Application for DNA Stretching", 2004, 4, 69-73.
Hashioka et al.: "Simple and Quick Detection of Target DNA by Hybridization in Nano Gap Channel Array." 9th International Conference on Miniaturized Systems or Chemistry and Life Sciences, vol. 1, pp. 730-732 (2005).
Henriquez et al.: "The resurgence of Coulter counting for analyzing nanoscale objects," The Analyst, 2004, 129, 478-482.
Hinds et al.: "Common deletions and SNPs are in linkage disequilibrium in the human genome," Nature Genetics 38: 82-85, 2006.
Howorka et al.: "Kinetics of duplex formation for individual DNA strands within a single protein nanopore," PNAS 98: 12996-13001, 2001.
Howorka et al.: "Sequence-specific detection of individual DNA strands using engineered nanopores," Nature Biotechnology 19: 636-639, 2001.
International Preliminary Report on Patentability dated Feb. 23, 2009 for PCT Application No. PCT/US2007/016408.
International Search Report and Written Opinion dated Jan. 19, 2009 for PCT Application No. PCT/US2008/058671.
International Search Report and Written Opinion dated Oct. 9, 2010 for PCT Application No. PCT/US2009/049244.
International Search Report dated Apr. 7, 2011 for PCT Application No. PCT/US2010/053513 filed Oct. 21, 2010.
International Search Report dated Aug. 16, 2010 for PCT Application No. PCT/US2009/064996.
International Search Report dated Aug. 17, 2012 for Application PCT/US2011/057115.
Japanese Office Action dated Jul. 24, 2012 for Japanese Patent Application No. 2009-520847 (English translation thereof is enclosed).
Jo et al.: "A single-molecule barcoding system using nanoslits for DNA analysis." Proc. Natl. Acad. Sci., 104(8):2673-2678 (2007).
Johansson et al.: "Primary vs. secondary neoplasia-associated chromosomal abnormalities-balanced rearrangements vs genomic imbalances?" Genes, Chromosomes and Cancer 16: 155-163, 1996.
Kasianowicz et al.: "Characterization of individual polynucleotide molecules using a membrane channel," PNAS 93: 13770-13773, 1996.

(56) References Cited

OTHER PUBLICATIONS

Koppal et al.: "Spanning the Drug Pipeline," Drug Discovery & Development, Sep. 13, 2005, 1 page, http://www.dddmag.com.
Kuhn et al., "Labeling of unique sequences in double-stranded DNA at sites of vicinal nicks generated by nicking endonucleases." Nucleic Acids Research, 36(7):e40:1-10 (2008).
Li et al.: "Ion-beam sculpting at nanometer length scales," Nature 412: 166-169, 2001.
Li et al.: "DNA molecules and configurations in a solid-state nanopore microscope," Nature Materials 2: 611-615, 2003.
Li, et al.: "Sacrificial polymers for nanofluid channels in biological applications," Nanotechnology, 2003, 14, 578-583.
Mannion et al., Conformational Analysis of Single DNA Molecule Undergoing Entropically Induced Motion in Nanochannels, Biophysical Journal, Jun. 2006, vol. 90, pp. 4538-4545.
McCarroll et al.: "Common deletion polymorphisms in the human genome," Nature Genetics 38: 86-92, 2006.
McGee et al.: "New In Vitro, Modeling Tools May Cut Tox Attrition," Drug Discovery & Development, Aug. 4, 2005, 4 pages, http://wvvw.dddmag.com.
McGee, et al.: "Small-Animal Models Advance in Vivo ADME-Tox", Drug Discovery & Development, Jul. 5, 2005, 3 pages, http://wvvw.dddmag.com.
Meller et al.: "Rapid nanopore discrimination between single polynucleotide molecules," PNAS 97: 1079-1084, 2001.
Meller et al.: "Voltage-Driven DNA Translocations through a Nanopore," Physical Review Letters 86: 3435-3438, 2001.
Meng et al.: "Optical mapping of lambda bacteriophage clones using restriction endonucleases," Nat Genet 9: 432-438, 1995.
Mijatovic et al., "Technologies for nanoflui di csystems: top-down vs. bottom-up—a review," Lab on a Chip, Royal Society of Chemistry, Cambridge, GB, Jan. 2005, vol. 5, 492-500.
Molecular Devices website, product page for Axopatch 200B: No date present NB/ http://www.moleculardevices.com/pages/instruments/cn_axopatch200b.html.
Nagata et al.: "Degradation of chromosomal DNA during apoptosis," Cell Death and Differentiation 10: 108-116, 2003.
Nath et al.: "A System for Micro/Nano Fluidic Flow", Diagnostics, 2005, Biomedical Microdevices, 7, 169-177.
Notice of Allowance dated Dec. 11, 2013 for Canadian Patent Application No. 2658122.
Notice of Allowance dated Jan. 23, 2014 for Australian Patent Application No. 2007338862.
Notice of Allowance dated Sep. 18, 2013 in U.S. Appl. No. 13/001,697.
Office Action dated Aug. 28, 2014 issued in European Patent Application No. 09774334.8.
Office Action dated Aug. 12, 2014 issued in Korean Patent Application No. 10-2009-7022447.
Office Action dated Dec. 9, 2013 for Japanese Patent Application No. 2009-520847.
Office Action dated Feb. 10, 2015 for Australian Patent Application No. AU2009267086.
Office Action dated Feb. 24, 2014 for Chinese Patent Application No. 200980125335.3.
Office Action dated Feb. 26, 2014 for Chinese Patent Application No. 201310189106.6.
Office Action dated Feb. 5, 2013 for Japanese Patent Application No. 2009-520847.
Office Action dated Jan. 14, 2014 for Japanese Patent Application No. 2011-516813 dated Jan. 14, 2014.
Office Action dated Oct. 14, 2014 for Japanese Patent Application No. 2011-516813 dated Oct. 14, 2014.
Office Action dated Jan. 4, 2012 for Chinese Patent Application No. 200780034694.9.
Office Action dated Jan. 7, 2015 for Australian Application No. 2011316989.
Office Action dated Jan. 7, 2015 for Australian Patent Application No. 2011316989.
Office Action dated Mar. 25, 2014 in Chinese Patent Application No. 201310054745.1.
Office Action dated Dec. 18, 2014 in Chinese Patent Application No. 201180060380.2.
Office Action dated Mar. 28, 2013 for Canadian Patent Application No. 2658122.
Office Action dated May 13, 2014 for Japanese Patent Application No. 2011-537585.
Office Action dated May 9, 2012 for Australian Patent Application No. 2007338862.
Office Action dated May 9, 2012 of U.S. Appl. No. 13/001,697.
Office Action dated Nov. 14, 2014 for Chinese Patent Application No. 201310189106.6.
Office Action dated Nov. 5, 2012 for Chinese Patent Application No. 200780034694.9.
Office Action dated Sep. 29, 2014 for Canadian Patent Application No. 2682275.
Office Action dated Jan. 20, 2015 for Japanese Patent Application No. 2013-258107.
Office Action in U.S. Appl. No. 13/710,180, dated Mar. 14, 2014.
Office Action in U.S. Appl. No. 13/880,365, dated Dec. 8, 2014.
Office Action dated Jan. 30, 2015 for Korean patent application No. 10-2011-7000192.
Office Action dated Apr. 15, 2015 for Canadian Patent Application No. 2682275.
Olivier et al., "High-throughput genotyping of single nucleotide polymorphisms using new biplex invader technology." Nucleic Acids Research, vol. 30, No. 12, p. E53 (2002).
Phillips et al., "Application of single molecule technology to rapidly map long DNA and study the conformation of stretched DNA." Nucleic Acids Research, 33(18):5829-5837 (2005).
Piepenburg et al., "DNA detection using recombination proteins." PLOS Biology, vol. 4, No. 7, e204 (2006).
Purves et al.: "Genotoxicity testing: Current Practices and Strategies Used by the Pharmaceutical I ndustry," Mutagenesis, 1995, vol. 10 No. 4 pp. 297-312.
Reccius et al., "Compression and free expansion of single DNA molecules in nanochannels." Physical Review Letters, 95:268101-1 (2005).
Reccius et al.: "Compression and Free Expansion of Single DNA Molecules in Nanochannels," Phys. Rev. Letts., Dec. 21, 2005, 95, 268101-1-268101-4.
Reil et al.: "Clinical validation of a new triplex real-time polymerase chain reaction assay for the detection and discrimination of Herpes simplex virus types 1 and 2", The Journal of Molecular Diagnostics: Jul. 2008, vol. 10, No. 4, pp. 361-367.
Turner, et al.: "Monolithic nanofluid sieving structures for DNA manipulation", Journal of Vacuum Science and Technology, 16, 3835, 1998.
Slater, et al., "Bidirectional Transport of Polyelectrolytes Using Self-Modulating Entropic Ratchets," Physical Review Letters, The American Physical Society, 78(6), Feb. 1997, 1170-1173.
Storm et al.: "Fabrication of solid-state nanopores with single-nanometer precision," Nature Materials 2: 537-540, 2003.
Storm et al.: "Fast DNA Translocation through a Solid-State Nanopore," Nano Letters 5: 1193-1197, 2005.
Technology Research News, LLC, "Melted fibers make nano channels," Jan. 14, 2004, Retrieved from the internet at URL <http://www.trnmag.com/Stories/2004/011404/Me I ted_fibers_$_l$ _make_ nano_channe I s_Brief.
Tegenfeldt et al., "From the Cover: The dynamics of genomic-length DNA molecules in 100-nm channels." Proc. Natl. Acad. Sci. USA, 101(30):10979-83 (2004).
Tegenfeldt et al.: "Micro and nanofluidics for DNA analysis," Anal Bioanal Chem 378: 1678-1692, 2004.
Tegenfeldt et al.: "The dynamics of genomic-length DNA molecules in 100-nm channe I s," PNAS 101: 10979-10983, 2004b.
Vaandrager et al.: "DNA fiber fluorescence in situ hybridization analysis of immunoglobulin class switching in B-cell neoplasia: aberrant CH gene arrangements in follicle center-cell lymphoma", Blood, Oct. 15, 1998, vol. 92, No. 8, pp. 2871-2878.

(56) References Cited

OTHER PUBLICATIONS

Volkmuth et al.: "DNA electrophoresis in microlithographic arrays", Department of Physics, Princeton University, Nature, vol. 358, Aug. 13, 1992, pp. 600-602.
Wade et al.: "The Quest for the $1,000 Human Genome" The New York Times, Jul. 18, 2006.
Wong et al.: "Deformation of DNA molecules by hydrodynamic focusing," J Fluid Mechanics 497: 55-65, 2003.
Written Opinion and Search Report of Intellectual Property Office of Singapore dated Jan. 9, 2013 for Singapore Patent Application No. 201009665-0.
Written Opinion dated Apr. 21, 2011 for PCT Application No. PCT/US2010/053513.
Xiao et al., "Rapid DNA mapping by fluorescent single molecule detection." Nucleic Acids Research, 35(e16):1-12 (2007).
Chen et al., A Microfluidic System for Saliva-Based Detection of Infectious Diseases, Ann. N.Y. Acad. Sci., 2007. 1098. pp. 429-436.
Kaufman et al.: "Early S phase DNA replication: A search for target of carcinogenesis" Advan. Enzyme Regul. 2007, 47: 127-138.
Pfannschmidt et al., Jan. 30, 1998, Superhelix organization by DNA curvature as measured through site-specific labeling, Journal of Molecular Biology, 275(4):601-611.
Rigby et al., Jun. 15, 2977, Labeling deoxyribonucleic acid to high specific activity in vitro by nick translation with DNA polymerase 1, Journal of Molecular Biology, 113(1):237-251.
Examination Report dated Feb. 1, 2016 in European patent application No. 07872156.0.
Examination Report dated Jul. 15, 2016 in European patent application No. 07872156.0.
Notice of Reasons for Refusal dated May 10, 2016 in Japanese patent application No. 2014-089510.
Patent Examination Report No. 1 dated Feb. 12, 2016 in Australian patent application No. 2014256367.
Office Action dated Nov. 27, 2015 for Canadian Patent Application No. 2682275.
Office Action dated Feb. 15, 2016 for Chinese Patent Application No. 201310189106.6.
Office Action dated Oct. 26, 2016 for Chinese Patent Application No. 201310189106.6.
Decision of Patent Grant dated Nov. 24, 2015 for Japanese Patent Application No. 2013-258107.
Examination Report dated May 11, 2015 in Canadian patent application No. 2729159.
Office action dated Apr. 14, 2016 in U.S. Appl. No. 13/765,353.
Examination Report dated Aug. 12, 2016 in European patent application No. 13179160.0.
Office Action dated Jan. 5, 2016 for Chinese Patent Application No. 200980125335.3.
Office Action dated Jul. 5, 2016 for Chinese Patent Application No. 200980125335.3.
Examination Report dated Dec. 15, 2015 in European patent application No. 09774334.8.
Examination Report dated Dec. 15, 2015 for European patent application No. 13179160.0.
Examination Report dated Aug. 12, 2016 for European patent application No. 13179160.0.
Notice of Reasons for Refusal dated Feb. 23, 2016 in Japanese patent application No. 2015-078505.
Notice of Reasons for Refusal dated Sep. 6, 2016 in Japanese patent application No. 2015-078505.
Supplemental Notice of Allowance dated Nov. 27, 2013 in U.S. Appl. No. 13/001,697.
Canadian Official Action dated Nov. 4, 2015 in Canadian patent application No. 2,744,064.
Chinese Office Action dated Aug. 8, 2016 for Chinese Patent Application No. 201410584764.X.
Examination Report dated Feb. 8, 2016 in Australian patent application No. 2011316989.
Examination Report dated Jul. 21, 2016 in European patent application No. 11777008.1.
Notice of Reasons for Refusal dated Nov. 17, 2015 in Japanese patent application No. 2013-535092.
Final Decision of Rejection dated Jun. 28, 2016 in Japanese patent application No. 2013-535092.
Office Action dated Dec. 15, 2015 in U.S. Appl. No. 13/880,365.
Office Action dated Jul. 11, 2016 in U.S. Appl. No. 13/880,365.
Official Action (Request) dated Jan. 28, 2016 in Russian patent application No. 2013117936.
Churchman et al., "Single molecule high-resolution colocalization of Cy3 and Cy5 attached to macromolecules measures intramolecular distances through time", PNAS, vol. 102, No. 5, Feb. 1, 2005, pp. 1419-1423.
Gordon et al., "Single-molecule high-resolution imaging with photobleaching", PNAS, vol. 101, No. 17, Apr. 27, 2004, pp. 6462-6465.
Toprak et al., "New Fluorescent Tools for Watching Nanometer-Scale Conformational Changes of Single Molecules", Annu. Rev. Biophys. Biomol. Struct., vol. 36, 2007, pp. 349-369.
Office Action dated Dec. 22, 2016 in Canadian Application No. 2,744,064.
Office Action dated Apr. 20, 2017 in Chinese Application No. 201410584764.X with English Translation.
Summons to attend oral proceedings dated Feb. 24, 2017 in European Application No. 07872156.0.
Summons to attend oral proceedings dated Feb. 7, 2017 2017 in European patent application No. 09774334.8.
Summons to attend oral proceedings dated Mar. 24, 2017 in European patent application No. 13179160.0.
EPO Form 2036 Notice on Hearing dated Sep. 21, 2017 in European Application No. 07872156.0.
Decision to refuse a European Patent application dated Oct. 12, 2017 in European Patent App. No. 07 872 156.0.

Figure 1a
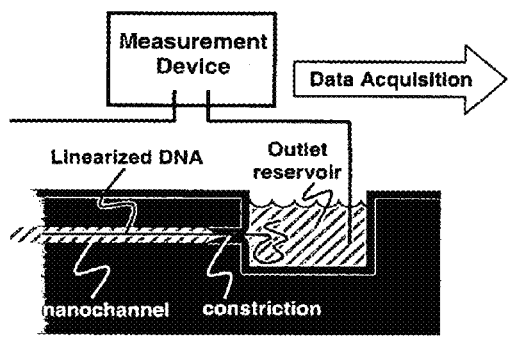
Figure 1c
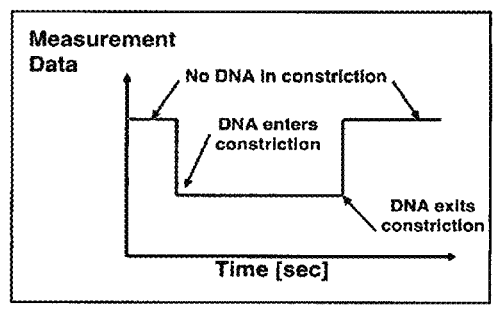
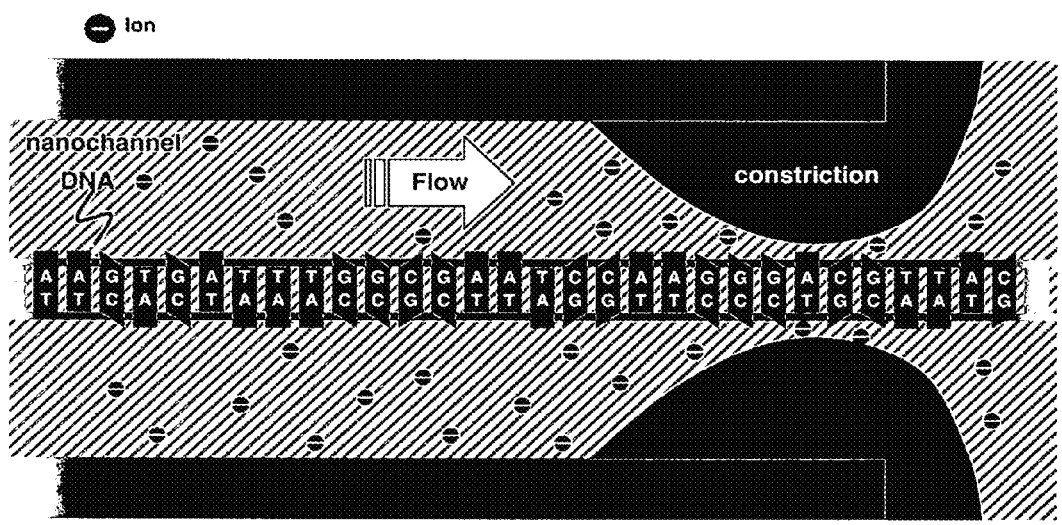
Figure 1b

Figure 2a
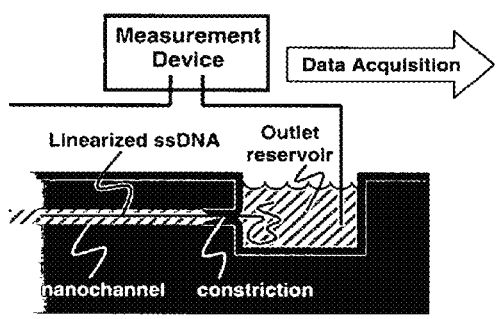
Figure 2c
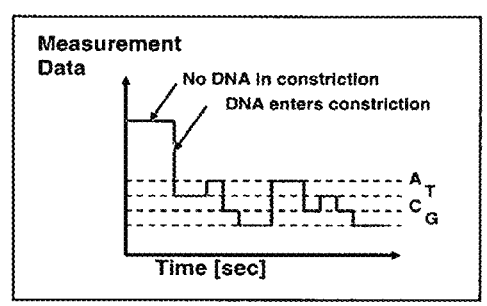
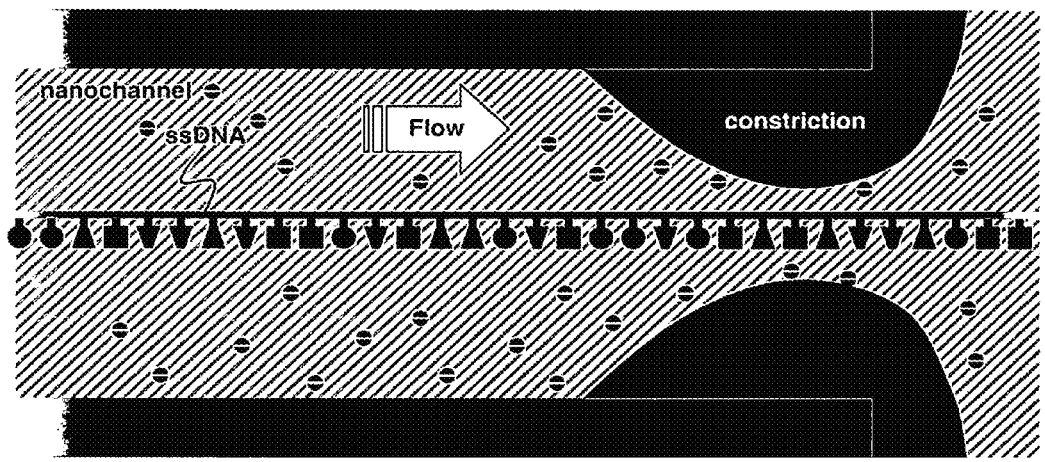
Figure 2b

Figure 3a
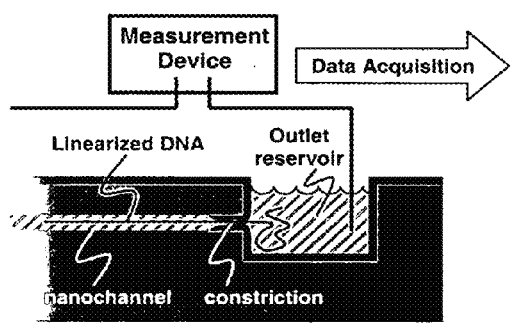
Figure 3c
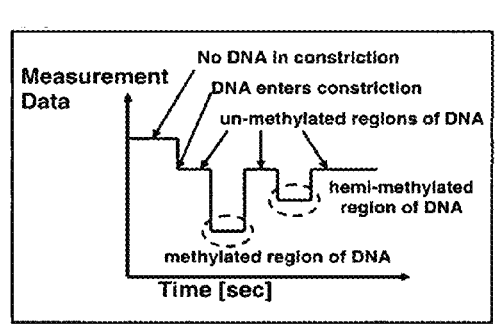
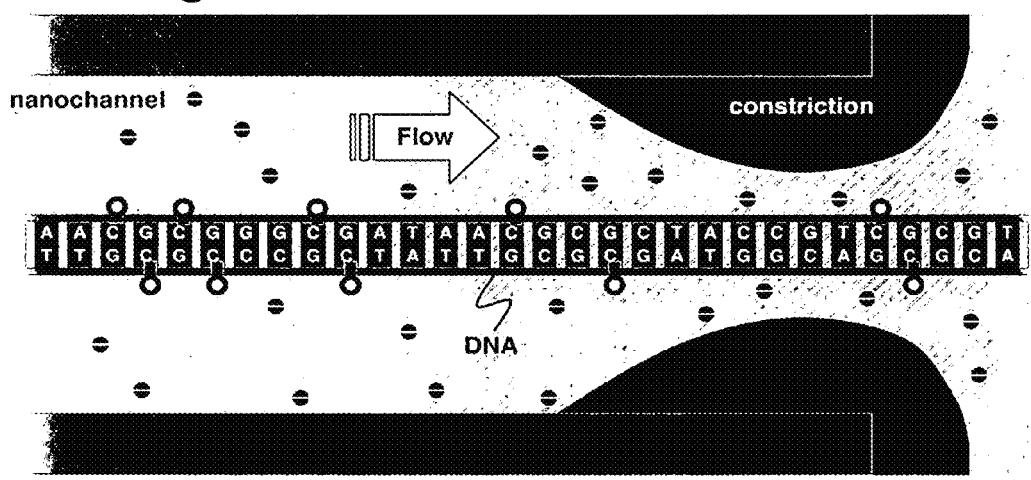
Figure 3b

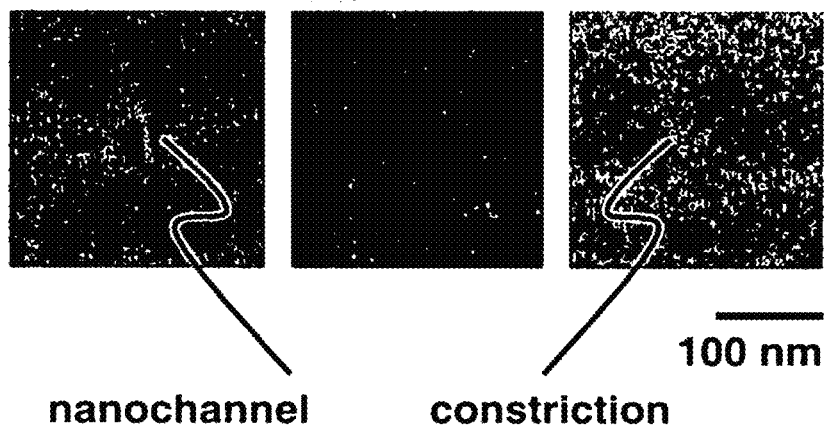

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 1
aagtgatttg gcgaatccaa gggacgttac                                        30

<210> SEQ ID NO 2
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 2
gtaacgtccc ttggattcgc caaatcactt                                        30

<210> SEQ ID NO 3
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 3
aacgcgggcg ataacgcgct accgtcgcgt                                        30

<210> SEQ ID NO 4
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 4
acgcgacggt agcgcgttat cgcccgcgtt         30

NANONOZZLE DEVICE ARRAYS: THEIR PREPARATION AND USE FOR MACROMOLECULAR ANALYSIS

CROSS REFERENCE TO RELATED APPLICATIONS

This application is a divisional of U.S. application Ser. No. 12/374,141, filed on Dec. 10, 2009, now issued as U.S. Pat. No. 9,061,901; which is the U.S. National Phase under 35 U.S.C. §371 of International Application No. PCT/US2007/016408 entitled "NANONOZZLE DEVICE ARRAYS: THEIR PREPARATION AND USE FOR MACROMOLECULAR ANALYSIS," filed on Jul. 19, 2007, designating the U.S.; which claims the benefit of U.S. Provisional Application No. 60/831,772, filed Jul. 19, 2006; U.S. Provisional Application No. 60/908,582, filed Mar. 28, 2007; and U.S. Provisional Application No. 60/908,584, filed Mar. 28, 2007, the entireties of these related applications are incorporated by reference herein.

FIELD OF THE INVENTION

The present invention pertains to the field of nanoscale devices. The present invention also pertains to the field of macromolecular sequencing, particularly the field of DNA sequencing and characterization.

BACKGROUND OF THE INVENTION

Various scientific and patent publications are referred to herein. Each is incorporated by reference in its entirety.

Biomolecules such as DNA or RNA are long molecules composed of nucleotides, the sequence of which is directly related to the genomic and post-genomic gene expression information of an organism. In most cases, the mutation or rearrangement of the nucleotide sequences during an individual's life span can lead to disease states such as genetic abnormalities or cell malignancy. In other cases, the small amount of sequence differences among each individual reflects the diversity of the genetic makeup of the population. Because of these differences in genetic sequence, certain individuals respond differently to environmental stimuli and signals, including drug treatments. For example, some patients experience positive response to certain compounds while others experience no effects or even adverse side effects.

The fields of population genomics, medical genomics and pharmacogenomics studying genetic diversity and medical pharmacological implications require extensive sequencing coverage and large sample numbers. The sequencing knowledge generated would be especially valuable for the health care and pharmaceutical industry. Cancer genomics and diagnostics study genomic instability events leading to tumorigenesis. All these fields would benefit from technologies enabling fast determination of the linear sequence of biopolymer molecules such as nucleic acids, or epigenetic biomarkers such as methylation patterns along the biopolymers. There is a long felt need to use very little amount of sample, even as little as a single cell. This would greatly advance the ability to monitor the cellular state and understand the genesis and progress of diseases such as the malignant stage of a cancer cell.

Most genome or epigenome analysis technologies remain too expensive for general analysis of large genomic regions for a large population. In order to achieve the goal of reducing the genomic analysis cost by at least four orders of magnitude, the so-called "$1000 genome" milestone, new technologies for molecular analysis methods are needed. See "The Quest for the $1,000 Human Genome," by Nicholas Wade, *The New York Times*, Jul. 18, 2006.

One technology developed for fast sequencing involves the use of a nanoscale pore through which DNA is threaded. Historically, the "nanopore" concept used a biological molecular device to produce ionic current signatures when RNA and DNA strands are driven through the pore by an applied voltage. Biological systems, however, are sensitive to pH, temperature and electric fields. Further, biological molecules are not readily integrated with the semiconductor processes required for sensitive on-chip electronics.

Many efforts have been since focused on designing and fabricating artificial nanopores in solid state materials. These methods, however, which are capable of producing only pores in membranes are not capable of producing longer channels needed to achieve true single-molecule sequencing of long biological polymers such as DNA or RNA.

Accordingly, there is a need in the field for devices capable of yielding sequence and other information for long biological polymers such as DNA or RNA.

SUMMARY OF THE INVENTION

In meeting the described challenges, in a first aspect the present invention provides methods for characterizing one or more features of a macromolecule, comprising linearizing a macromolecule residing at least in part within a nanochannel, at least a portion of the nanochannel being capable of physically constraining at least a portion of the macromolecule so as to maintain in linear form that portion of the macromolecule, and the nanochannel comprising at least one constriction; transporting at least a portion of the macromolecule within at least a portion of the nanochannel such that at least a portion of the macromolecule passes through the constriction; monitoring at least one signal arising in connection with the macromolecule passing through the constriction; and correlating the at least one signal to one or more features of the macromolecule.

In a second aspect, the present invention provides devices for analyzing a linearized macromolecule, comprising two or more fluid reservoirs; and a nanochannel comprising a constriction, the nanochannel placing the at least two fluid reservoirs in fluid communication with one another.

Further provided are methods for transporting a macromolecule, comprising providing at least two fluid reservoirs; providing an at least partially linearized macromolecule, at least a portion of the macromolecule residing in a nanochannel, the nanochannel placing the at least two reservoirs in fluid communication with one another, the nanochannel comprising a constriction; and applying a gradient to the macromolecule, the gradient giving rise to at least a portion of the linearized macromolecule being transported within at least a portion of the nanochannel.

Additionally provided are methods for fabricating a constricted nanochannel, comprising providing a nanochannel; the nanochannel having an internal diameter in the range of from about 0.5 nm to about 1000 nm, and the nanochannel having a length of at least about 10 nm; reducing the internal diameter of the nanochannel either at a location within the nanochannel, at a location proximate to the end of the nanochannel, or both, so as to give rise to a constriction within or adjacent to the nanochannel, the constriction having an internal diameter in fluidic communication with the nanochannel, the nanochannel being capable of maintaining a linearized macromolecule in its linearized form, and the reduced internal diameter being capable of permitting the passage of at least a portion of a linearized macromolecule.

Also disclosed are methods for linearizing a macromolecule, comprising placing a macromolecule in a nanochannel, at least a portion of the nanochannel being capable of physically constraining at least a portion of the macromolecule so as to maintain in linear form that portion of the macromolecule.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 1a is a schematic view of a DNA sequencer showing linearized double-stranded DNA passing through a nanochannel into an outlet reservoir, where a measurement device detects physical, chemical, electrical, or other changes in the outlet reservoir or within the nanochannel related to the passage of the DNA;

FIG. 1b depicts a DNA molecule flowing through a nanonozzle constriction at the end of a nanochannel, wherein the DNA molecule is a double-stranded DNA having a first strand comprising a nucleic acid sequence of SEQ ID NO: 1 and a complementary strand comprising a nucleic acid sequence of SEQ ID NO: 2;

FIG. 1c depicts the data evolved from the passage of the DNA through the constricted nanochannel;

FIG. 2a is a schematic view of a DNA sequencer showing linearized single-stranded DNA passing through a nanochannel into an outlet reservoir, where a measurement device detects any physical, chemical, electrical, or other changes in the outlet reservoir or within the nanochannel related to the passage of the DNA;

FIG. 2b depicts single-stranded DNA molecule flowing through a nanonozzle constriction at the end of a nanochannel;

FIG. 2c depicts the data evolved as individual nucleotides of the single-stranded DNA pass through the constriction of the nanochannel;

FIG. 3a is a schematic view of a DNA sequencer showing linearized, methylated double-stranded DNA passing through a nanochannel into an outlet reservoir, where a measurement device detects any physical, chemical, electrical, or other changes in the outlet reservoir or within the nanochannel related to the passage of the DNA;

FIG. 3b depicts the methylated double-stranded DNA molecule flowing through a nanonozzle constriction at the end of a nanochannel, wherein the methylated double-stranded DNA molecule is a double-stranded DNA having a first strand comprising a nucleic acid sequence of SEQ ID NO: 3 and a complementary strand comprising a nucleic acid sequence of SEQ ID NO: 4;

FIG. 3c depicts the data evolved as individual nucleotides of the methylated double-stranded DNA pass through the constriction of the nanochannel;

(FIG. 7b) self-terminating opening of the constriction using an acid etchant terminated by exposure to a neutralizing strong base; and (FIG. 7c) the final nanonozzle device after the etchant and neutralizer are removed;

(FIG. 8a) a sacrificial macromolecule is placed into the nanochannel and allowed to partially exit into the reservoir; (FIG. 8b) the fluid is removed and material is deposited around the sacrificial molecule; and (FIG. 8c) the sacrificial molecule is removed leaving a constriction at the end of the nanochannel; and FIG. 9a, FIG. 9b and FIG. 9c present a series of three scanning electron micrographs that describes the gradual reduction in size of a channel opening using additive deposition of material: (FIG. 9a) additive deposition of silicon oxide on an open nanochannel of initial width and height of about 150 nm leads to an enclosed nanochannel of about 50 nm diameter, (FIG. 9b) variation of the deposition of parameters leads to smaller enclosed channels, and (FIG. 9c) by extension, a sub-10 nm opening can be created.

DETAILED DESCRIPTION OF ILLUSTRATIVE EMBODIMENTS

Terms

Figure 4:
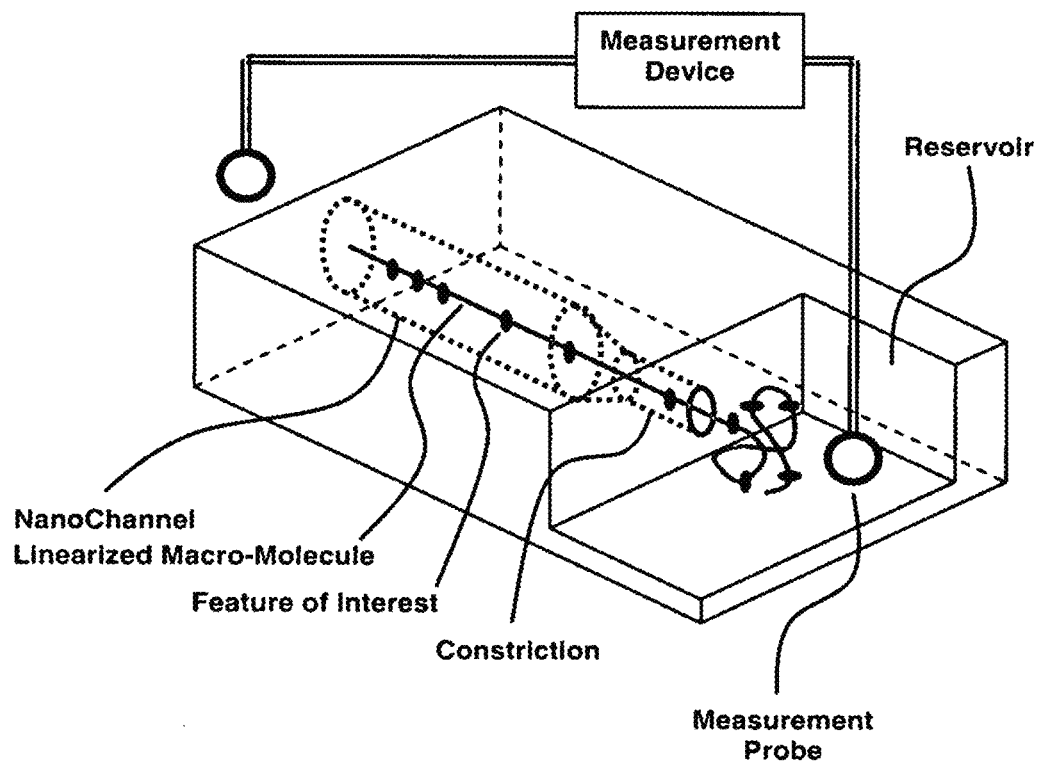
FIG. 4 depicts an representative embodiment of an enclosed nanochannel in communication with a reservoir, the nanochannel having a constriction of cross-sectional area smaller than remainder of nanochannel, and macromolecules being linearized within the nanochannel and features of interest on the molecule being detected as they pass through the constriction.

As used herein, the term "substantially linear" means that the conformation of at least a portion of a long molecule, such as, but not limited to, a polynucleic acid comprising 200 nucleic acids linked together, does not loop back on itself or does not containing any sharp bends or curves greater than about 360 degrees.

As used herein, the term "nanochannel" means a conduit, channel, pipe, duct, or other similar structure having at least one nanoscale dimension.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one aspect, the present invention provides methods for characterizing one or more features of a macromolecule. These methods include linearizing a macromolecule residing at least in part within a nanochannel, at least a portion of the nanochannel being capable of physically constraining at least a portion of the macromolecule so as to maintain in linear form that portion of the macromolecule.

Suitable nanochannels have a diameter of less than about twice the radius of gyration of the macromolecule in its extended form. A nanochannel of such dimension is known to begin to exert entropic confinement of the freely extended, fluctuating macromolecule coils so as to extend and elongate the coils. Suitable nanochannels can be prepared according to the methods described in Nanochannel Arrays And Their Preparation And Use For High-Throughput Macromolecular Analysis, U.S. patent application Ser. No. 10/484,293, filed Jan. 20, 2004, the entirety of which is incorporated by reference herein.

Suitable nanochannels include at least one constriction. Such constrictions function to locally reduce the effective inner diameter of the nanochannel. Constrictions can be sized so as to permit the passage of linearized macromolecules.

The methods also include the step of transporting at least a portion of the macromolecule within at least a portion of the nanochannel such that at least a portion of the macromolecule passes through the constriction. This is shown in, for example, FIGS. 1b, 2b, and 3b, in which DNA is shown passing through a nanochannel constriction. Constrictions can be made, for example by depositing material at the end of a nanochannel to seal off the nanochannel, and then etching away a portion of the deposited material until a pore much narrower than the nanochannel is produced. This is further illustrated in FIGS. 6 to 9.

Where a comparatively long macromolecule is to be analyzed, the end of the macromolecule is delivered into one end of the nanochannel. This is accomplished by, for example, gradient structures, that assist such delivery into a nanochannel; suitable gradient structures are described in U.S. Pat. No. 7,217,562, to Cao, et al.

The methods also include monitoring at least one signal arising in connection with the macromolecule passing through the constriction; and correlating the at least one signal to one or more features of the macromolecule. This is depicted in FIGS. 1a, 2a, and 3a, which depict a schematic of monitoring a signal arising in connection with the passage of a macromolecule through a constriction in a nanochannel. Suitable signals include, for example, electric charge signals, optical signals, electromagnetic signals, magnetic signals, or any combination thereof. Electrical signals can be monitored using, for example, any of a variety of commercially available current meters and amplifiers. For example, suitable signal monitoring equipment is capable of applying a constant voltage in the range of from about a nanovolt, or a microvolt, or a millivolt, or even a volt or more across electrodes in contact with liquid within the reservoirs and nanochannel segment. Suitable monitoring equipment is also capable of measuring current between the electrodes many times persecond. Suitable equipment will have a bandwidth of at least about 100 Hertz ("Hz", cycles per second), or about 1 kilohertz ("kHz"), or about 10 kHz, or about 100 kHz, or about 1 megahertz ("MHz"), or even about 10 megahertz. Accordingly, current can be made once measurements are variations on the order of the nanosecond, or the microsecond, or even on the millisecond scale. Current amplitude can be from pico seconds . . . . Translocation speed of a sDNA can be around 40 bases per microsecond through a typical "patch clamp amplifier". Best machine today can sample once every microseconds. Axopatch 200B, Molecular Devices (www.moleculardevices.com), having a bandwidth of 100 KHz, is capable of 100,000 current measurements per second, or equivalent to 10 microseconds per current measurement of a change in the current between the electrodes connected to the two waste reservoirs.

Macromolecules suitable for the present method include polynucleotides, polynucleosides, natural and synthetic polymers, natural and synthetic copolymers, dendrimers, surfactants, lipids, natural and synthetic carbohydrates, natural and synthetic polypeptides, natural and synthetic proteins, or any combination thereof. DNA is considered a particularly suitable macromolecule that can be analyzed according to the methods as discussed elsewhere herein.

A macromolecule analyzed according to the methods as provided herein typically resides within a fluid. Suitable fluids include water, buffers, cell media, and the like. Suitable fluids can also be electrolytic, acidic, or basic.

Transporting the macromolecule is accomplished by exposing the macromolecule to a gradient, the gradient suitably applied along the flow direction of a suitable nanochannel. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a gradient of hydrophobicity, a capillary flow, or any combination thereof. An electric field is a particularly suitable gradient.

The gradient may be temporally constant, spatially constant, or any combination thereof. The gradient may also vary in space and time as needed. In some embodiments, varying the gradient enables the transportation of the macromolecule in both forward and reverse directions. In some embodiments, varying the gradient permits the same portion of the macromolecule to be passed through the constriction multiple times.

Varying the gradient also enables the user to advance the macromolecule quickly through the constriction until a region of particular interest on the macromolecule is reached, in a manner analogous to fast-forwarding a cassette tape to a desired selection. Once the region of interest is reached, the gradient may be varied so as to pass the region of interest through the constriction at a lower speed. The gradient may also be reversed to effect a reverse movement of the macromolecule through the restriction. This would be analogous to rewinding the cassette tape to a desired position. Accordingly, "play", "fast forward", "rewind", "pause" and "stop" functions can arise by controlling the magnitude and polarity of the gradient between the reservoirs.

Suitable signals that can be detected include a visual signal, an infrared signal, an ultraviolet signal, a radioactive signal, a magnetic signal, an electrical signal, an electromagnetic signal, or any combination thereof. Electrical signals are considered preferable for the reason that they are easily monitored, but other signals may be effectively monitored.

The macromolecule may include one or more labels; suitable labels include electron spin resonance molecule, a fluorescent molecule, a chemiluminescent molecule, an isotope, a radioisotope, an enzyme substrate, a biotin molecule, an avidin molecule, an electrical charge-transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, a nucleic acid, a carbohydrate, an antigen, a hapten, an antibody, an antibody fragment, a lipid, a polymer, an electrically charged particle, a modified nucleotide, a chemical functional group, a chemical moiety, or any combination thereof. In some embodiments, the label is a chemical moiety such as a methyl group. This is shown in non-limiting fashion at FIG. 3b, which depicts a DNA strand labeled with several methyl groups and the detection of those methyl groups as indicative of the presence of one or more particular features of the labeled DNA.

Signals are, in some embodiments, inherently emitted by the macromolecule. Such inherently emitted signals include magnetic signals or radioactive signals, where the macromolecule or portions of the macromolecule are magnetic or radioactive. Where the signal is inherently emitted by the macromolecule, it may not also be necessary to illuminate the macromolecule so as to elicit a detectable signal.

In other embodiments, the signal is generated by illuminating the molecule. Illumination includes exposing at least a portion of the macromolecule to visible light, ultraviolet light, infrared light, x-rays, gamma rays, electromagnetic radiation, radio waves, radioactive particles, or any combination thereof. Suitable illumination devices include coherent and incoherent sources of light which can illuminate, excite, or even scatter from the macromolecule. UV, VIS, IR light sources can be used, such as lasers and other light surfaces.

Features of macromolecules detected by the disclosed methods include the size of the macromolecule, the molecular composition of the macromolecule, the molecular sequence of the macromolecule, an electrical property of one or more molecules of the macromolecule, a chemical property of one or more molecules of the macromolecule, a radioactive property of one or more molecules of the macromolecule, a magnetic property of one or more molecules of the macromolecule, or any combination thereof.

As discussed elsewhere herein, macromolecules are, in some embodiments, labeled. Accordingly, a feature of such macromolecule is the location of one or more labels of the macromolecule.

The molecular composition of a molecule is also characterized by the instant methods. The molecular composition includes the position of one or more molecules of the macromolecule, DNA polymorphisms, DNA copy number polymorphisms, amplifications within DNA, deletions within DNA, translocations within DNA, inversions of particular loci within DNA, the location of a methyl group within the macromolecule, or any combination thereof. Polymorphisms are, in some embodiments, detected by observing the presence of a labeled probe that is complementary only to that polymorphism.

The detection of binding sites between a drug and the macromolecule, macromolecule-drug complexes, DNA repairing sites, DNA binding sites, DNA cleaving sites, SiRNA binding sites, anti-sense binding sites, transcription factor binding sites, regulatory factor binding sites, restriction enzyme binding sites, restriction enzyme cleaving sites, or any combination thereof are all included within the present invention.

As discussed elsewhere herein, such features are determined by interrogating the macromolecule for the presence of one or more probes complementary to the features of interest. The methods are shown schematically in FIGS. 1c 2c, and 3c, each of which depicts the monitoring of a signal arising in connection with the passage of the macromolecule through the nanochannel constriction. In some embodiments, two or more probes are used to determine two or more features of a given macromolecule.

Certain embodiments of the device include a plurality of nanochannels. Such arrays of nanochannels are useful in efficiently characterizing multiple features of a single macromolecule or multiple features of multiple macromolecules. It will be apparent to one having ordinary skill in the art that labels complementary to certain features can be chosen and then applied to a given macromolecule that is then characterized to determine whether such features are present on that given macromolecule.

Also disclosed are devices for analyzing a linearized macromolecule. Suitable devices include two or more fluid reservoirs and a nanochannel comprising a constriction and the nanochannel placing the at least two fluid reservoirs in fluid communication with one another. As described elsewhere herein, suitable nanochannels are capable of physically constraining at least a portion of macromolecule so as to maintain that portion in linear form. This is set forth in further detail in U.S. Application No. 60/831,772, filed Jul. 19, 2006; U.S. Application No. 60/908,582, filed on Mar. 28, 2007, and U.S. Application No. 60/908,584, filed Mar. 28, 2007, the entirety of each of the aforementioned patent applications is incorporated by reference herein. Suitable devices with reservoirs can be made using standard silicon photolithographic and etching techniques. Nanochannel length can also be controlled using such techniques. Reservoirs and associated microfluidic regions, including the microfluidic interfacing regions, can be sealed using a standard wafer (Si wafer-Si wafer) bonding techniques, such as thermal pbonding, adhesive bonding of a transparent lid (e.g., quartz, glass, or plastic).

The constriction suitably resides at one end of the nanochannel. In some embodiments, however, the constriction resides within the nanochannel. The ultimate location of the constriction will depend on the user's needs. Constrictions inside a nanochannel can be made as follows: using a sacrificial material as a filler as described further herein (see, e.g., Example 7 discussed further below).

Suitable nanochannels have a length in the range of at least about 10 nm, or at least about 15 nm, or at least about 20 nm, at least about 30 nm, at least about 50 nm, or even at least about 100 nm, at least about 500 nm, or at least about 1000 nm. In some embodiments, the nanochannel comprises a length at least equal to about the length of the linearized macromolecule.

Suitable nanochannels also have an effective inner diameter in the range of from about 0.5 nm to about 1000 nm, or in the range of from about 10 nm to about 500 nm, or in the range of from about 100 nm to about 300 nm, or in the range of from about 150 nm to about 250 nm. Nanochannel effective inner diameters can also be at least about 15 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm. As discussed, the nanochannel comprises an effective inner diameter capable of maintaining the macromolecule in linearized form.

The terms "effective inner diameter" and "inner diameter" are used interchangeably unless indicated otherwise. The term "effective inner diameter" refers not only to nanochannels having a circular cross-sectional area, but also to nanochannels having non-circularly shaped cross sectional areas. For example, the "effective inner diameter" can be determined by assuming the nanochannel has a circular cross section, and forcing the actual cross sectional area of the nanochannel to be effectively calculated in terms of the area of a circle having an effective inner diameter: Cross Sectional Area of Nanochannel=pi×(effective inner diameter/2)$^2$. Accordingly, the effective inner diameter of a nanochannel can be determined as:

Effective Inner Diameter=2[(Cross Sectional Area of Nanochannel)/pi]$^{1/2}$

Constrictions suitably have an effective inner diameter or effective dimension permitting molecular transport in the range of from about 0.5 nm to about 100 nm; or in the range of from about 1 to about 80 nm, or in the range of from about 5 to about 50 nm, or in the range of from about 8 nm to about 30 nm, or in the range of from about 10 nm to about 15 nm. Suitable constrictions have an effective inner diameter capable of maintaining a linearized macromolecule passing across the constriction in linearized form. The effective inner diameter or dimension can be controlled by controlling the etching conditions, or by controlling the size of the sacrificial material within the constriction region.

The disclosed devices also include a gradient, such gradients suitably existing along at least a portion of the nanochannel. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof.

In some embodiments, the gradient is capable of linearizing at least a portion of a macromolecule residing within at least a portion of the nanochannel. In preferred embodiments, however, the gradient is capable of transporting at least a portion of a macromolecule located within the nanochannel along at least a portion of the nanochannel.

The devices suitably include a gradient generator capable of supplying the described gradient. Suitable generators include a voltage source, a magnet, an acoustic source, a pressure source, or any combination thereof.

The gradient generator is suitably capable of applying a constant gradient. The gradient generator is also, in some embodiments, capable of applying a variable gradient. The examples set forth elsewhere herein provide additional detail. It will be apparent to one having ordinary skill in the art that the intensity and variability of the gradient will be chosen according to the user's needs.

The two or more fluid reservoirs of the device comprise the same fluid in some embodiments. In other embodiments, the two or more fluid reservoirs comprise different fluids. In some embodiments, the different fluids may be used to themselves provide the gradient used to transport the macromolecule within the nanochannel—fluids of differing ionic strength or other property may be chosen to provide such a gradient. Suitable fluids include buffers, acids, bases, electrolytes, cell media, surfactants, and the like.

The devices also include a detector capable of detecting a signal arising from at least a portion of the linearized macromolecule passing through the constriction. Suitable detectors include a charge coupled device (CCD) detection system, a complementary metal-oxide semiconductor (CMOS) detection system, a photodiode detection system, a photo-multiplying tube detection system, a scintillation detection system, a photon counting detection system, an electron spin resonance detection system, a fluorescent detection system, a photon detection system, an electrical detection system, a photographic film detection system, a chemiluminescent detection system, an enzyme detection system, an atomic force microscopy (AFM) detection system, a scanning tunneling microscopy (STM) detection system, a scanning electron microscopy (SEM) detection system, an optical detection system, a nuclear magnetic resonance (NMR) detection system, a near field detection system, a total internal reflection (TIRF) detection system, a patch clamp detection system, an electrical current detection system, an electrical amplification detection system, a resistance measurement system, a capacitive detection system, and the like.

Suitable detectors are capable of monitoring one or more locations within one or more of the fluid reservoirs, or, in other embodiments, are capable of monitoring a location within the nanochannel, or even a location proximate to an end of the nanochannel. It will be apparent to the user that employing one or more detectors capable of detecting different signals at different locations would enable characterization of multiple features of a given macromolecule.

In some embodiments, the devices include an illuminator. Illuminators suitable include a laser, a source of visible light, a source of radioactive particles, a magnet, a source of ultraviolet light, a source of infrared light, or any combination thereof. The illuminator is used, in some embodiments, to excite a portion of the macromolecule within the nanochannel. As a non-limiting example, a source of light of a certain wavelength is used to excite fluorescent labels residing at certain, specific locations on the macromolecule so as to elicit the presence of such labels.

The devices also suitably include a data processor. In some embodiments, the devices include a data recorder. Such processors are used to manipulate and correlate large data sets.

Figure 5:
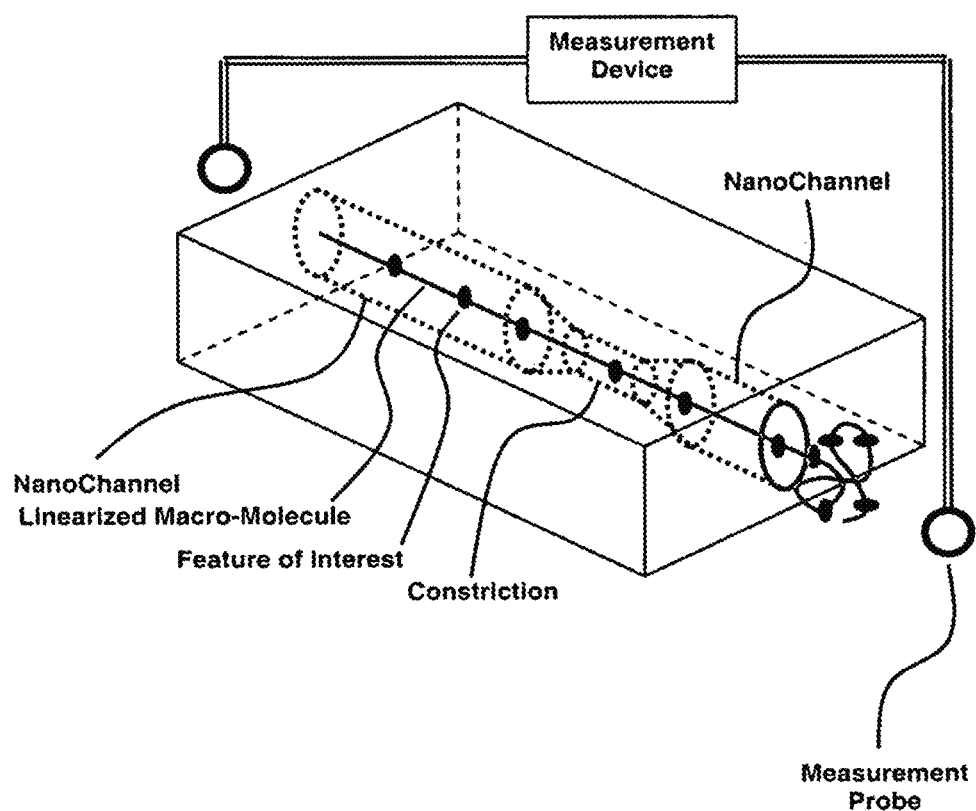
FIG. 5 depicts an enclosed nanochannel in communication with a second nanochannel via a constriction of cross-sectional area smaller than both nanochannels, macromolecules are linearized within the nanochannel and features of interest on the molecule are detected as they pass through the constriction.

One embodiment of the disclosed devices is shown in FIG. 4, which depicts a nanochannel constricted at one end proximate to a reservoir and a detector monitoring a signal arising out of a reservoir into which a macromolecule is linearly transported. Another embodiment is shown in FIG. 5, in which a constriction connects two nanochannels. In FIG. 5, it is seen that the detector monitors one or more signals evolved across the constricted nanochannel assembly.

As discussed elsewhere herein, where a comparatively long macromolecule is to be analyzed, one end of the macromolecule is first transported into one end of the nanochannel. As discussed, this may be accomplished by, for example, gradient structures, that assist such delivery; suitable gradient structures are described in U.S. Pat. No. 7,217,562, to Cao, et al., the entirety of which is incorporated by reference herein.

Also disclosed are methods for transporting a macromolecule. Such methods include providing at least two fluid reservoirs and providing an at least partially linearized macromolecule at least a portion of the macromolecule residing in a nanochannel. As discussed elsewhere herein, the macromolecule may be linearized by confinement in a suitably-dimensioned nanochannel having an inner diameter of less than about twice the radius of gyration of the linearized macromolecule.

Suitable nanochannels place the reservoirs in fluid communication with one another. Suitable nanochannels, as described elsewhere herein, also include a constriction. The dimensions of suitable constrictions are described elsewhere herein.

The methods also include the application of a gradient to the macromolecule. The gradient suitably gives rise to at least a portion of the linearized macromolecule being transported within at least a portion of the nanochannel. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof. The gradient may suitably by constant or vary, depending on the needs of the user.

The reservoirs are generally larger in volume than that of the nanochannel segments. The reservoirs can be of almost any shape and size. For example, a reservoir may be circular, spherical, rectangular, or any combination thereof. The size of a reservoir will be dictated by the user's needs and may vary.

The nanochannels of the disclosed method have a length of greater than about 10 nm, or greater than about 12 nm, or greater than about 14 nm, or greater than about 16 nm, or greater than about 18 nm, or greater than about 20 nm, or greater than about 25 nm, or greater than about 30 nm, or greater than about 35 nm, or greater than about 40 nm, or greater than about 45 nm. In some embodiments, the nanochannels have a length of greater than about 100 nm or even greater than about 500 nm. Suitable nanochannels can also be greater than about 1 micron in length, or greater than about 10 microns, or greater than about 100 microns, or greater than about 1 mm, or even greater than about 10 mm in length. In some embodiments, the length of the nanochannel is chosen to exceed about the length of the linearized macromolecule.

Further disclosed are methods for fabricating constricted nanochannels. These methods first include providing a nanochannel. Suitable nanochannels have an effective internal diameter in the range of from about 0.5 nm to about 1000 nm, or in the range of from about 1 nm to about 500 nm, or in the range of from about 5 nm to about 100 nm, or in the range of from about 10 nm to about 15 nm. Nanochannel effective inner diameters can also be at least about 15 nm, or at least about 20 nm, or at least about 30 nm, or at least about 40 nm, or at least about 50 nm, or at least about 60 nm, or at least about 70 nm, or at least about 80 nm, or at least about 90 nm, or at least about 100 nm.

The methods also include the step of reducing the effective internal diameter of the nanochannel either at a location within the nanochannel, at a location proximate to the end of the nanochannel, or both, so as to give rise to a constriction within or adjacent to the nanochannel, the constriction having an internal diameter in fluidic communication with the nanochannel. Sample constrictions are shown in FIG. 1b, FIG. 4, FIG. 5, and FIG. 6. Suitable nanochannels are capable of maintaining a linearized macromolecule in its linearized form; as discussed elsewhere herein, this is suitably accomplished by using nanochannel segments of suitable dimensions so as to physically constrain the macromolecule to maintain the macromolecule in substantially linear form. The reduced internal diameter of the constricted nanochannel is suitably capable of permitting the passage of at least a portion of a linearized macromolecule.

Figures 6A, 6B:
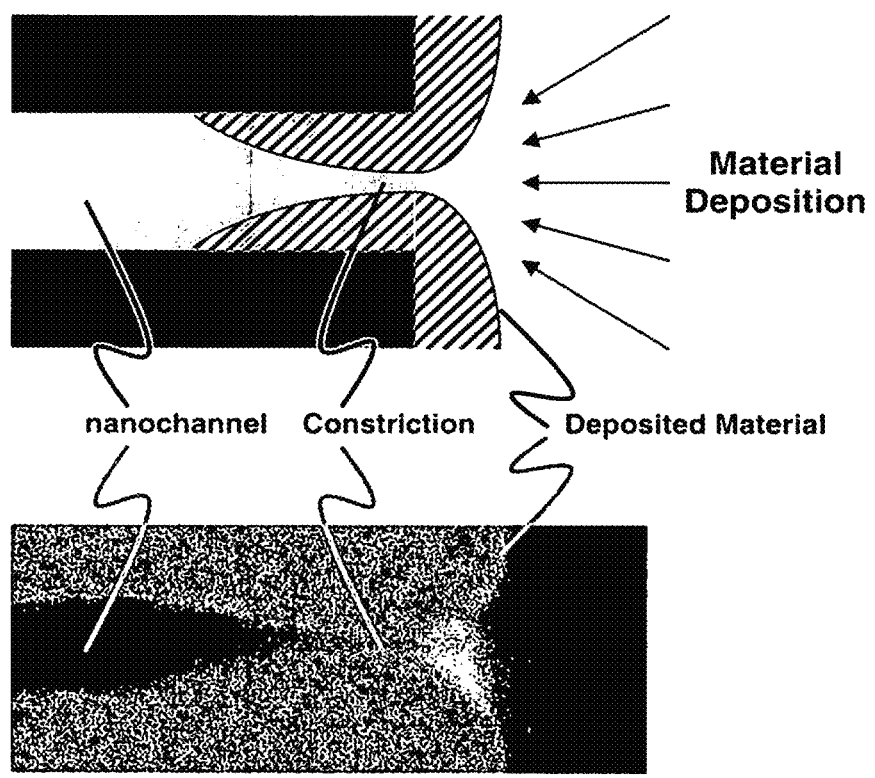
FIG. 6a depicts the preparation of a constriction at the end of a nanochannel by additive material deposition.
FIG. 6b is a scanning electron micrograph of an embodiment of such a constriction at the end of a nanochannel.

In one embodiment, the internal diameter of the nanochannel is reduced so as to form the constriction by additively depositing one or more materials within, or exterior to, the nanochannel. This is suitably accomplished by sputtering, spraying, physical vapor deposition, chemical vapor deposition, or any combination thereof. In some embodiments, the additive deposition ceases before the nanochannel is completely occluded. This is depicted in FIGS. 6a and 6b, where the deposition of additive material proximate to one end of a nanochannel is shown, the deposition ceasing before the nanochannel is completely occluded. Such a nanochannel is also shown in FIG. 9, in which the reduction in effective inner diameter is seen as the end of the nanochannel (FIG. 9a) is reduced by varied deposition (FIGS. 9b and 9c) of additive material.

Figure 7A:
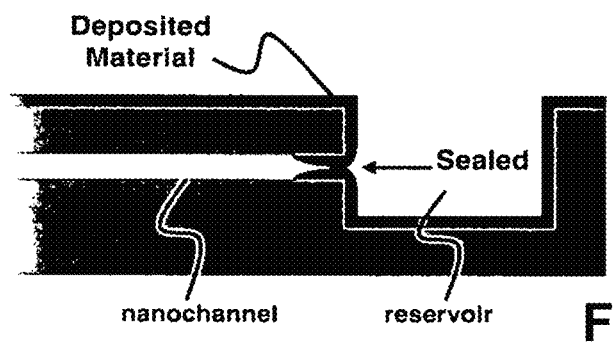
FIG. 7a, FIG. 7b and FIG. 7c depict a representative fabrication of a constriction at the end of a nanochannel by (FIG. 7a) deposition of material at the end of the nanochannel resulting in complete sealing of the channel.
Figure 7B:
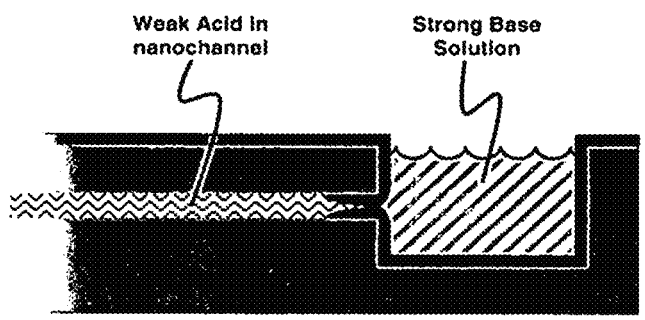
Figure 7C:
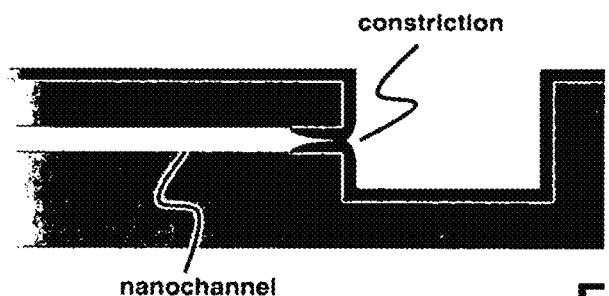

In other embodiments of the invention, the additive deposition ceases after the nanochannel is completely occluded. In these embodiments, the methods include the step of re-opening the sealed nanochannel by removing at least a portion of the deposited additive material. This is suitably accomplished by etching. The etching process entails contacting one side of deposited additive material with an first species capable of etching the deposited additive material and contacting the other side of the deposited additive material with a second species capable of retarding the etching activity of the etch species upon contact with the first species. In some embodiments, the second species is capable of halting the etching activity of the etch species upon contact with the first species. This is depicted in FIG. 7a, where sealing material is applied at one end of a nanochannel and then, FIG. 7b, etched away by a strongly basic solution, the etching ceasing, FIG. 7c, when the basic solution etches through the sealing material and is neutralized by the strong acid residing on the opposite side of the sealing material. As will be apparent to those having ordinary skill in the art, the conditions in the nanochannel, the relative amounts of the first and second species, and other operating parameters will be adjusted so as to achieve the desired diameter.

In still other embodiments, reducing the internal diameter of the nanochannel includes several steps: (FIG. 8a) placing a sacrificial material within the nanochannel, (FIG. 8*b*) depositing additive material proximate to the sacrificial material so as to fully occlude the nanochannel, and (FIG. 8*c*) selectively removing at least a portion of the sacrificial material while leaving essentially intact the proximate additive material so as to give rise to a reduced internal diameter of the nanochannel of the dimension of the removed sacrificial material. It will be apparent to those having ordinary skill in the art that this aspect of the present invention is useful for fabricating voids having a variety of dimensions within nanoscale and larger channels or within other structures. DNA and carbon nanotubes are both considered suitable sacrificial materials. Other materials that may be selectively dissolved or etched away will be apparent to those having ordinary skill in the art.

The present invention also provides methods for linearizing macromolecules so as to constrain the degrees of freedom of the macromolecules from three dimensions to essentially one dimension. These methods include placing a macromolecule in a nanochannel, at least a portion of the nanochannel being capable of physically constraining at least a portion of the macromolecule so as to maintain in linear form that portion of the macromolecule.

The nanochannels suitably include a constriction. Suitable dimensions for constrictions are described elsewhere herein.

The methods also include, in some embodiments, applying a gradient to the macromolecule, such that at least a portion of the macromolecule passes, linearly, through the nanochannel constriction. Suitable gradients include an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, or any combination thereof.

The microchannels of the disclosed methods suitable place two or more fluid reservoirs in fluid communication with one another.

The nanochannels suitable include an internal diameter of less than about two times the radius of gyration of the linear conformation of the macromolecule. Nanochannels suitably have lengths of at least about 10 nm, of at least about 50 nm, of at least about 100 nm, of at least about 500 nm. Suitable inner diameters for nanochannels are in the range of from about 0.5 nm to about 1000 nm, or in the range of from about 5 nm to about 200 nm, or in the range of from about 50 nm to about 100 nm.

EXAMPLES AND OTHER ILLUSTRATIVE EMBODIMENTS

The following are non-limiting examples and illustrative embodiments, and do not necessarily restrict the scope of the invention.

General Procedures.

Deposition of filling material was provided by sputtering, CVD, e-beam evaporation with a tilted sample wafer at various angles. This step was used to both reduce the nanochannel openings and create a tapered nozzle at the end of the channels.

Typically, to fabricate enclosed nanochannels, 100-340 nm of $SiO_2$ was deposited onto the channel openings. Effective sealing was achieved with various deposition conditions that were tested. At gas pressure of 30 mTorr, RF power of ~900 W, and DC bias of 1400 V, a deposition rate of ~9 nm/min was achieved. At lower pressure of 5 mTorr, the deposition rate was increased to an estimated 17 nm/min. Filling material was deposited on the nanochannel opening by sputtering at 5 mTorr. Further details about making nanochannel arrays and devices can be found in U.S. Patent Application Pub. Nos. US 2004-0033515 A1 and US 2004-0197843 A1, the entirety of which is incorporated by reference herein.

Example 1

A silicon substrate was provided having a plurality of parallel linear channels having a 150 nm trench width and a 150 nm trench height. These channel openings are sputtered at a gas pressure of 5 mTorr according to the general procedures given above. The sputter deposition time was 10-25 minutes to provide a nanochannel array that can either be partially sealed or completely sealed.

Example 2

This example provides an enclosed nanochannel array using an e-beam deposition technique. A substrate can be provided as in Example 1. Silicon dioxide can be deposited by an e-beam (thermo) evaporator (Temescal BJD-1800) onto the substrate. The substrate can be placed at various angles incident to the depositing beam from the silicon dioxide source target; the deposition rate can be set to about 3 nm/minute and 150 nm of sealing material can be deposited in about 50 minutes. The angle of the incident depositing beam of sealing material can be varied to reduce the channel width and height to less than 150 nm and 150 nm, respectively, and to substantially seal the channels by providing shallow tangential deposition angles.

Example 3

In this example, a nanochannel array can be contacted with a surface-modifying agent. A nanochannel array made according to Example 1 can be submerged in solution to facilitate wetting and reduce non-specific binding. The solution can contain polyethelyene glycol silane in toluene at concentrations ranging from 0.1-100 mM and remains in contact with the nanochannel array from about 1 hour to about 24 hours. Subsequent washing in ethanol and water is used to remove ungrafted material.

Example 4

This example describes a sample reservoir with a nanochannel array for a nanofluidic chip. A nanochannel array having 100 nm wide, 100 nm deep nanochannels was made according to general procedures of Example 1. The nanochannel array was spin-coated with a photoresist such as AZ-5214E and patterned by photolithography with a photomask using a Karl Suss MA6 Aligner to provide regions on opposite ends of the channel array for preparing the reservoirs. The exposed areas were etched using reactive ion etching in a Plasma-Therm 720SLR using a combination of $CF_4$ and $O_2$ at a pressure of 5 mTorr and RF power of 100 W with an etch rate of 20 nm/min to expose the nanochannel ends and to provide a micron-deep reservoir about a millimeter wide on the opposite ends of the channels at the edge of the substrate.

Example 5

This example describes filling a nanofluidic chip with a fluid containing DNA macromolecules to analyze DNA. A cylindrical-shaped plastic sample-delivery tube of 2 mm diameter was placed in fluid communication with one of the reservoirs of the nanochannel array of Example 3. The delivery tube can be connected to an external sample delivery/collection device, which can be in turn connected to a pressure/vacuum generating apparatus. The nanochannels are wetted using capillary action with a buffer solution. A buffer solution containing stained for example lambda phage macromolecules (lambda DNA) were introduced into the nanochannel array by electric field (at 1-50 V/cm); the solution concentration was 0.05-5 microgram/mL and the lambda DNA was stained at a ratio of 10:1 base pair/dye with TOTO-1 dye (Molecular Probes, Eugene, Oreg.). This solution of stained DNA was diluted to 0.01-0.05 microgram/mL into 0.5×TBE (tris-boroacetate buffer at pH 7.0) containing 0.1M of an anti-oxidant and 0.1% of a linear polyacrylamide used as an anti-sticking agent.

Example 6

This example describes the fabrication of a nanonozzle at end of nanochannel using acid etching. Fabrication of the nanonozzle device begins with a completed silicon nanochannel having enclosed nanochannels as provided in Example 1. Creation of the nanopore proceeds by sputter coating a thin layer of chromium over the exposed end of the channel. Sputter coating using a Temescal system can be controlled with sub-nm precision with deposition amounts of 5-200 nm at a rate of 0.01-1 nm/sec or until the end of the nanochannel is completely covered with chromium. A wet-etch process can then be employed to open a sub-10 nm pore in the chromium. A dilute chromium etchant such as $Cr^{-7}$ can be flowed into the channel using capillary forces or other forms of pumping. Dilution can range from 1× to 10,000×. Because $Cr^{-7}$ is a highly selective acid etchant, it will preferentially react with the chromium at the end of the channel rather than the silicon channels themselves. To stop the etch once a pore has opened, the area outside the channel will be filled with a highly concentrated base solution (such as sodium hydroxide) that will rapidly neutralize the weak acid upon break-through. After subsequent washing of the device, the result will be a nanoscale nozzle at the end of a nanochannel.

Example 7

Figure 8A:
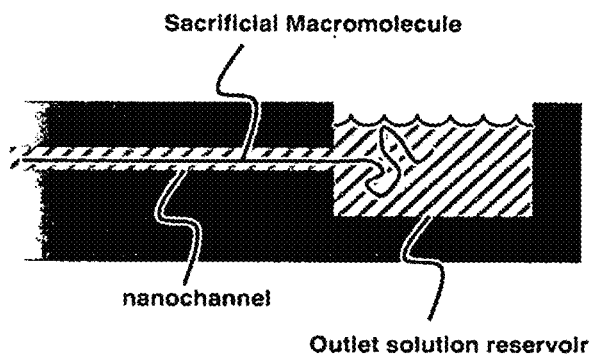
FIG. 8a, FIG. 8b and FIG. 8c depict a representative fabrication of a constriction at the end of a nanochannel using sacrificial material.
Figure 8B:
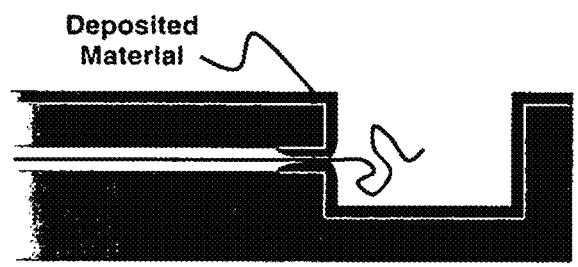
Figure 8C:
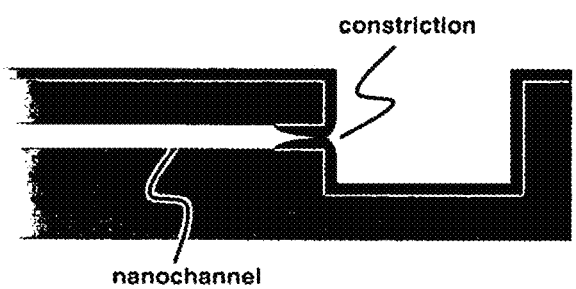

This example describes how to fabricate a nanonozzle chip using a sacrificial macromolecule. A nanofluidic chip with input/output fluid reservoirs connected by nanochannels is used to linearize double strand DNA (FIG. 8a). In this example, long fragments of DNA, approximately 1-10 Mbp in length, uniformly stained with YOYO-1 is preferable. The concentration of the DNA should be around 0.5 micrograms/mL, with the dye stained to a ratio of 10:1 base pair/dye. The buffer solution is composed of 0.5×TBE (tris-boroacetate buffer at pH 7.0) containing 0.1M of an anti-oxidant and 0.1% of a linear polyacrylamide used as an anti-sticking agent. Using the nanofluidic chip and procedure described previously (Cao 2002), the solution of sacrificial DNA molecules are flowed into the nanochannels of the chip, where they exit the nanochannels at the outlet reservoir. Using a fluorescent imaging microscope, the exit of the DNA molecules is observed in real time, and their movement controlled by applying an electric field across the reservoirs (1-50 V/cm). With such a scheme, a desired DNA fragment's position can be suspended having only partially exited the nanochannel. The nanochannel chip is then dried at 50° C. in vacuum environment removing any residual buffer solution, so that the DNA fragment of interest remains partially inside the nanochannel. Interaction between the nanochannel surface and the DNA fragment, such as through van der Waals bonding, maintains the fragment's position in the channel during the drying process.

After the nanochannel chip has been dried, a material such as silicon dioxide is deposited over the surface of the chip (FIG. 8b) such that the entrance to the nanochannel becomes blocked, and the DNA fragment enclosed. The rate of material deposition and the temperature of the deposition must be carefully chosen such that the DNA fragment is not damaged during this process. Evaporating material at 0.2 A/s or less on a sample kept at −160° C. using a cooling stage has been shown to protect small organic molecules from damage (Austin 2003). In order to obtain uniform coverage around the nanochannel to properly form a nanonozzle, the stage is rotated and tilted during the evaporation process. To completely close a nanochannel of 80 nm in diameter, approximately 200 nm of silicon dioxide material should be evaporated.

Example 8

Operation of a Device—Electrical Measurement for Sequencing Single-Stranded Nucleic Acid A voltage bias is applied across a nanochannel device having a constriction (either nanogate or nanonozzle) approximately 1.5 nm inner diameter placed at one end of the nanochannel, the nanochannel being about 200 microns in length, for a single strand nucleic acid for sequencing using electrodes (can be copper, silver, titanium, platinum, gold, or aluminum) contacting reservoirs at each end of the nanochannel, the reservoirs having dimensions of about 5-100 microns in diameter and 1-2 microns deep. The electrodes are deposited into the reservoirs and lead lines leading to outside the fluidic region for connection to a current monitor. A voltage range of 100 mV-100V can be used. Biological buffer (TE, TBE, TAE) is placed in each reservoir, capillary action and a pressure differential aids in wetting the nanofluidic device using a suitable fluidic delivery pump or syringe. A nucleic acid sample (e.g., 100 base sDNA and up, at least 1000 bases, or 10000 bases, or 100000 bases, or 1 million, or even 10 million, or even 100 million, up to chromosomal length) in buffer solution (1 nanoliter up to about 100 microliters) is delivered to one or both of the reservoirs. A gradient is applied to aid in the transport of one or more polynucleic acid molecules into the nanochannel in into the constriction. A field is applied, specifically in this example, a controlled voltage gradient to apply a current from one reservoir, throughout the nanochannel, through the constriction with the polynucleic acid residing within the constriction, and into the second reservoir. The electrical current flowing through this system is detected and amplified using an Axopatch 200B (Molecular Devices) patch clamp amplifier. Typical measured currents range from about 100 fA to about 1 uA with fluctuations approximately hundreds of picoamps as the DNA moves through the constriction. Labels attached to the single strand DNA can produce additional current fluctuations of magnitude smaller than that created by the DNA itself. For the case of measurements with a spatial resolution of a single base, typical translocation speed is such that the measurement system can register a minimum of 1 measurement per base. In the case of the Axopatch 200B with 100 kHz bandwidth, the maximum translocation speed is 100 kB/sec, assuming 50% stretching of the DNA molecule in the nanochannel. This gives rise to a translocation speed of the DNA through the construction to be about 0.015 nm/microsec. The measure current differences are measured and correlated to a seet of calibration standards to give rise to the sequence of the DNA sample.

A sample table tabulating suitable cross-sectional dimensions for the analysis of various target molecules is shown below:

TABLE

| Target Molecule Analyzed | Minimum cross-sectional dimension of Constriction (nm) |
| --- | --- |
| ss-DNA | 1.5 |
| ss-DNA + complementary strands | 2 |
| ds-DNA with nick, gap or lesion | 2 |
| ds-DNA | 2 |
| ds-DNA + moiety (eg. Methyl group, labeling group) | 2.1 |
| ds-DNA + small compound | 2.5 |
| ds-DNA + 3rd strand probe | 3.5 |
| ds-DNA + biotin | 5 |
| ds-DNA + protein bound factors (eg. Transcription factors) | 4-15 |
| ds-DNA + bead (eg. Quantum dot, magnetic beads) | 10-50 |

What is claimed:

1. A method for characterizing one or more features of a macromolecule, comprising:
   linearizing the macromolecule residing at least in part within a nanochannel, said macromolecule comprising a label,
      at least a portion of the nanochannel being capable of physically constraining at least a portion of the macromolecule so as to maintain in linear form that portion of the macromolecule, and
      wherein a first effective inner diameter of the nanochannel is between about 10 nm and about 500 nm, the nanochannel comprising at least one constriction that is configured to locally reduce the effective inner diameter to a second effective inner diameter of about 0.5 nm to about 100 nm, whereby the second effective inner diameter is less than the first effective inner diameter; and
   transporting at least a portion of the macromolecule within at least the portion of the nanochannel such that at least the portion of the macromolecule passes through the constriction;
   monitoring at least one signal arising in connection with the label of the macromolecule passing through the constriction,
   wherein the at least one signal characterizes one or more features of the macromolecule.

2. The method of claim 1, wherein the macromolecule is selected from the group consisting of: a polynucleotide, a polynucleoside, a polymer, a copolymer, a dendrimer, a surfactant, a lipid, a carbohydrate, a polypeptide, a protein, and any combination thereof.

3. The method of claim 1, wherein the macromolecule resides within a fluid.

4. The method of claim 1, wherein the transporting comprises exposing the macromolecule to a gradient.

5. The method of claim 4, wherein the gradient is selected from the group consisting of: an electroosmotic field, an electrophoretic field, a magnetic field, an electric field, an electromagnetic field, a flow field, a radioactive field, a mechanical force, an electroosmotic force, an electrophoretic force, an electrokinetic force, a temperature gradient, a pressure gradient, a surface property gradient, a capillary flow, and any combination thereof.

6. The method of claim 1, wherein the at least one signal is selected from the group consisting of: a visual signal, an infrared signal, an ultraviolet signal, a radioactive signal, a magnetic signal, an electrical signal, an electromagnetic signal, or any combination thereof.

7. The method of claim 1, wherein the macromolecule comprises two or more labels.

8. The method of claim 1, wherein a feature of the macromolecule comprises the location of one or more labels of the macromolecule.

9. The method of claim 8, further comprising the detection of sites selected from the group consisting of: binding sites between a drug and the macromolecule, macromolecule-drug complexes, DNA repairing sites, DNA binding sites, DNA cleaving sites, SiRNA binding sites, anti-sense binding sites, transcription factor binding sites, regulatory factor binding sites, restriction enzyme binding sites, restriction enzyme cleaving sites, and any combination thereof.

10. The method of claim 1, wherein the label is selected from the group consisting of: an electron spin resonance molecule, a fluorescent molecule, a chemiluminescent molecule, a radioisotope, and enzyme substrate, a biotin molecule, an avidin molecule, an electrical charged transferring molecule, a semiconductor nanocrystal, a semiconductor nanoparticle, a colloid gold nanocrystal, a ligand, a microbead, a magnetic bead, a paramagnetic particle, a quantum dot, a chromogenic substrate, an affinity molecule, a protein, a peptide, a nucleic acid, a carbohydrate, an antigen, a hapten, an antibody, an antibody fragment, a lipid, a polymer, an electrically charged particle, modified nucleotide, and any combination thereof.

11. The method of claim 1, wherein a feature of the macromolecule is selected from the group consisting of: the size of the macromolecule, the molecular composition of the macromolecule, the molecular sequence of the macromolecule, an electrical property of one or more molecules of the macromolecule, a chemical property of one or more molecules of the macromolecule, a radioactive property of one or more molecules of the macromolecule, a magnetic property of one or more molecules of the macromolecule, and any combination thereof.

12. The method of claim 11, wherein the molecular composition of the macromolecule is selected from the group consisting of: the position of one or more molecules of the macromolecule, DNA polymorphisms, DNA copy number polymorphisms, amplifications within DNA, deletions within DNA, translocations within DNA, inversions of particular loci within DNA, the location of a methyl group within the macromolecule, and any combination thereof.

13. The method of claim 1, wherein a ratio of the second effective inner diameter to the first effective inner diameter of the nanochannel is at most 40%.

14. A method for transporting a macromolecule, comprising:
   providing at least a first and a second fluid reservoir;
   providing an at least partially linearized macromolecule, at least a portion of the partially linearized macromolecule residing in a nanochannel, wherein a first effective inner diameter of the nanochannel is between about 10 nm and about 500 nm,
   the nanochannel placing the at least two reservoirs in fluid communication with one another,
   the nanochannel comprising a constriction in or at a terminal end of the nanochannel, said constriction configured to locally reduce the first effective inner diameter of the nanochannel to be about 0.5 nm to about 100 nm, whereby the second effective inner diameter is less than the first effective inner diameter; and applying a gradient to the partially linearized macromolecule,
the gradient giving rise to at least the portion of the partially linearized macromolecule being transported within at least a portion of the nanochannel and to the second fluid reservoir; and
detecting signals from the second reservoir, said signals arising from the partially linearized macromolecule that has been transported to the second reservoir.

15. The method of claim 14, wherein the nanochannel comprises a length greater than about 100 nm.

16. The method of claim 14, wherein the nanochannel comprises a length greater than about the length of the partially linearized macromolecule.

17. The method of claim 14, wherein the gradient is selected from the group consisting of: an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, and any combination thereof.

18. A method for linearizing a macromolecule, comprising:
placing the macromolecule in a nanochannel, wherein the nanochannel comprises a constriction in or at a terminal end of the nanochannel,
at least a portion of the nanochannel being capable of physically constraining at least a portion of the macromolecule so as to maintain in linear form that portion of the macromolecule,
wherein a first effective inner diameter of the nanochannel is between about 10 nm and about 500 nm, and wherein the constriction is configured to locally reduce the first effective inner diameter of the nanochannel to a second effective inner diameter that is less than about 40% of the first effective inner diameter, wherein the second effective inner diameter is less than the first effective inner diameter, whereby the macromolecule is linearized.

19. The method of claim 18, further comprising applying a gradient to the macromolecule, such that at least a portion of the macromolecule passes, linearly, through the nanochannel constriction.

20. The method of claim 19, wherein the gradient is selected from the group consisting of: an electroosmotic field, an electrophoretic field, capillary flow, a magnetic field, an electric field, a radioactive field, a mechanical force, an electroosmotic force, an electrophoretic force, an electrokinetic force, a temperature gradient, a pressure gradient, a surface property gradient, a capillary flow, and any combination thereof.

21. The method of claim 18, wherein the nanochannel places two or more fluid reservoirs in fluid communication with one another.

22. The method of claim 18, wherein the first effective inner diameter of the nanochannel is less than about two times the radius of gyration of the linear conformation of the macromolecule.

* * * * *